US012378606B2

(12) United States Patent
Frasch et al.

(10) Patent No.: US 12,378,606 B2
(45) Date of Patent: *Aug. 5, 2025

(54) PROBES AND METHODS FOR MEASURING TANDEM REPEATS

(71) Applicant: Arizona Board of Regents on Behalf of Arizona State University, Scottsdale, AZ (US)

(72) Inventors: Wayne Frasch, Phoenix, AZ (US); Fusheng Xiong, Phoenix, AZ (US)

(73) Assignee: Arizona Board of Regents on Behalf of Arizona State University, Scottsdale, AZ (US)

(*) Notice: Subject to any disclaimer, the term of this patent is extended or adjusted under 35 U.S.C. 154(b) by 874 days.

This patent is subject to a terminal disclaimer.

(21) Appl. No.: 17/498,643

(22) Filed: Oct. 11, 2021

(65) Prior Publication Data
US 2022/0195521 A1 Jun. 23, 2022

Related U.S. Application Data

(63) Continuation of application No. 16/886,205, filed on May 28, 2020, now Pat. No. 11,168,366, which is a continuation of application No. 16/089,887, filed as application No. PCT/US2017/025389 on Mar. 31, 2017, now Pat. No. 10,718,017.

(60) Provisional application No. 62/316,538, filed on Mar. 31, 2016.

(51) Int. Cl.
*C12Q 1/6876* (2018.01)
*C12Q 1/6827* (2018.01)
*C12Q 1/6851* (2018.01)
*C12Q 1/686* (2018.01)

(52) U.S. Cl.
CPC ......... *C12Q 1/6876* (2013.01); *C12Q 1/6827* (2013.01); *C12Q 1/6851* (2013.01); *C12Q 1/686* (2013.01); *C12Q 2521/319* (2013.01); *C12Q 2521/501* (2013.01); *C12Q 2525/151* (2013.01); *C12Q 2525/307* (2013.01); *C12Q 2545/114* (2013.01)

(58) Field of Classification Search
CPC .................. C12Q 1/68; C07H 21/00
See application file for complete search history.

(56) References Cited

U.S. PATENT DOCUMENTS

| 8,126,649 | B2 | 2/2012 | Frasch et al. | |
| 10,718,017 | B2* | 7/2020 | Frasch | C12Q 1/6851 |
| 11,168,366 | B2* | 11/2021 | Frasch | C12Q 1/6851 |
| 2007/0264646 | A1* | 11/2007 | Maki | C12N 7/00 435/235.1 |
| 2008/0131899 | A1* | 6/2008 | Landegren | C12Q 1/6848 435/6.12 |

FOREIGN PATENT DOCUMENTS

| WO | 2007089674 A2 | 8/2007 |
| WO | 2017173279 A1 | 10/2017 |

OTHER PUBLICATIONS

Geng et al., Single-Cell Forensic Short Tandem Repeat Typing within microfluidic droplets. Analytical Chemistry 86:703 (Year: 2014).*
Kuchta et al., Optimization of fluorescence measurement in duplex real-time PCR with TaqMan® probes labeled with VIC and quenched by TAMRA. Biotechniques 42(2) 147-149 (Year: 2007).*
Adleman, L., "Molecular Computation of Solutions to Combinatorial Problems", Science, Nov. 1994, vol. 266, No. 5187, pp. 1021-1024 <DOI:10.1126/science.7973651>.
Aubert, G. et al., "Telomeres and Aging", Physiological Reviews, 2008, vol. 88, pp. 557-579 <DOI:10.1152/physrev.00026.2007>.
Baird, D. et al., "Extensive allelic variation and ultrashort telomeres in senescent human cells", Nature Genetics, Feb. 2003 (published online Jan. 2003), vol. 33, pp. 203-207 <DOI:10.1038/ng1084>.
Blackburn, E., "Switching and signaling at the telomere", Cell, Sep. 2001, vol. 106, No. 6, pp. 661-673 <DOI:10.1016/S0092-8674(01)00492-5>.=.
Blackburn, E., "Telomere states and cell fates", Nature, Nov. 2000, vol. 408, pp. 53-56 <DOI:10.1038/35040500>.
Braich, R. et al., "Solution of a 20-Variable 3-SAT Problem on a DNA Computer", Science, Apr. 2002, vol. 296, No. 5567, pp. 499-502 <DOI:10.1126/science.1069528>.
Cawthon, R., "Telomere measurement by quantitative PCR", Nucleic Acids Research, May 2002, vol. 30, No. 10, article e47, 6 pages.
Ferlicot, S. et al., "Measurement of telomere length on tissue sections using quantitative fluorescence in situ hybridization (Q-FISH)", Journal of Pathology, Aug. 2003 (published online Jun. 2003), vol. 200, pp. 661-666 <DOI:10.1002/path.1392>.
Goronzy, J. et al., "Telomeres, immune aging and autoimmunity", Experimental Gerontology, Mar. 2006, vol. 41, No. 3, pp. 246-251 <DOI:10.1016/j.exger.2005.12.002>.
Hiyama, E. et al., "Telomere and telomerase in stem cells", British Journal of Cancer, Apr. 2007, vol. 96, pp. 1020-1024 <DOI:10.1038/sj.bjc.6603671>.
Kahng, A. et al., "Match twice and stitch: a new TSP tour construction heuristic", Operations Research Letters, Nov. 2004, vol. 32, No. 6, pp. 499-509 <DOI:10.1016/j.orl.2004.04.001>.
Kari, L. et al., "Using DNA to solve the Bounded Post Correspondence Problem", Theoretical Computer Science, Jan. 2000, vol. 231, No. 2, pp. 193-203 <DOI:10.1016/S0304-3975(99)00100-0>.
Kimura, M. et al., "Measurement of telomere length by the Southern blot analysis of terminal restriction fragment lengths", Nature Protocols, Sep. 2010, vol. 5, No. 9, pp. 1596-1607 <DOI:10.1038/nprot.2010.124>.

(Continued)

*Primary Examiner* — Ethan C Whisenant
(74) *Attorney, Agent, or Firm* — FULLER IP LAW LLC; Rodney J. Fuller

(57) ABSTRACT

The present disclosure relates to nucleic acid probes and kits for determining the length of a region of tandem repeats in a subject's genome and methods of using the DNA probes for determining the length of a region of tandem repeats in a subject's genome. In some embodiments, the region of tandem repeats in telomeres.

20 Claims, 11 Drawing Sheets

Specification includes a Sequence Listing.

(56) References Cited

OTHER PUBLICATIONS

Lansdorp, P. et al., "Heterogeneity in telomere length of human chromosomes", Human Molecular Genetics, May 1996, vol. 5, No. 5, pp. 685-691 <DOI:10.1093/hmg/5.5.685>.

Lee, J. et al., "Solving traveling salesman problems with DNA molecules encoding numerical values", Biosystems, Dec. 2004, vol. 78, No. 1-3, pp. 39-47 <DOI:10.1016/j.biosystems.2004.06.005>.

Lee, J. et al., "Temperature Gradient-Based DNA Computing for Graph Problems with Weighted Edges", 8th International Workshop on DNA-Based Computers, DNA8 (Sapporo, Japan, Jun. 2002), first online Jan. 2003, vol. 2568, pp. 73-84.

Lipton, RJ., "DNA Solution of Hard Computational Problems", Science, Apr. 1995, vol. 268, No. 5210, pp. 542-545 <DOI:10.1126/science.7725098>.

MacDonald, J. et al., "Medium Scale Integration of Molecular Logic Gates in an Automaton", Nano Letters, Oct. 2006, vol. 6, No. 11, pp. 2598-2603 <DOI:10.1021/nl0620684>.

Mahalakshmi, S. et al., "yciM is an essential gene required for regulation of lipopolysaccharide synthesis in *Escherichia coli*", Molecular Microbiology, 2014 (available online Nov. 2013, vol. 91, No. 1, pp. 145-157 DOI:10.1111/mmi.12452>.

Martens, U. et al., "Measurement of telomere length in haematopoietic cells using in situ hybridization techniques", Biochemical Society Transactions, Feb. 2000, vol. 28, No. 2, pp. 245-250 <DOI:10.1042/bst0280245>.

Moyzis, R. et al., "A Highly Conserved Repetitive DNA-Sequence, (Ttaggg)N, Present at the Telomeres of Human-Chromosomes", Proceedings of the National Academy of Sciences of the United States of America, Sep. 1988, vol. 85, No. 18, pp. 6622-6626 <DOI:10.1073/pnas.85.18.6622>.

Narath, R. et al., "Automatic telomere length measurements in interphase nuclei by IQ-FISH", Cytometry. Part A, Dec. 2005, vol. 68A, No. 2, pp. 113-120 <DOI:10.1002/cyto.a.20190>.

Ogihara, M. et al., "Simulating Boolean circuits on a DNA computer", Algorithmica, Jun. 1999, vol. 25, No. 2-3, pp. 239-250 <DOI:10.1007/PL00008276>.

O'Sullivan, J. et al., "Chromosomal instability in ulcerative colitis is related to telomere shortening", Nature Genetics, Oct. 2002 (published online Sep. 2002), vol. 32, pp. 280-284 <DOI:10.1038/ng989>.

Patent Cooperation Treaty, International Searching Authority, International Preliminary Report on Patentability and Written Opinion for PCT/US2017/025389, 5 pages, opinion mailed Jun. 27, 2017.

Patent Cooperation Treaty, International Searching Authority, International Search Report for PCT/US2017/025389, 4 pages, mailed Jun. 27, 2017.

Payne, S. et al., "Temporal control of self-organized pattern formation without morphogen gradients in bacteria", Molecular Systems Biology, Oct. 2013, vol. 9, No. 697, 10 pages <DOI:10.1038/msb.2013.55>.

Perner, S. et al., "Quantifying telomere lengths of human individual chromosome arms by centromere-calibrated fluorescence in situ hybridization and digital imaging", The American Journal of Pathology, Nov. 2003, vol. 163, No. 5, pp. 1751-1756 <DOI:10.1016/S0002-9440(10)63534-1>.

Qian, L. et al., "A simple DNA gate motif for synthesizing large-scale circuits", Journal of the Royal Society Interface, Sep. 2011 (published online Feb. 2011), vol. 8, No. 62, pp. 1281-1297 <DOI:10.1098/rsif.2010.0729>.

Qian, L. et al., "Neural network computation with DNA strand displacement cascades", Nature, Jul. 2011, vol. 475, pp. 368-372 <DOI:10.1038/nature10262>.

Qian, L. et al., "Scaling Up Digital Circuit Computation with DNA Strand Displacement Cascades", Science, Jun. 2011, vol. 332, No. 6034, pp. 1196-1201 <DOI:10.1126/science.1200520>.

Sakamoto, K. et al., "Molecular Computation by DNA Hairpin Formation", Science, May 2000, vol. 288, No. 5469, pp. 1223-1226 <DOI:10.1126/science.288.5469.1223>.

Spetzler, D. et al., "Heuristic Solution to a 10-City Asymmetric Traveling Salesman Problem Using Probabilistic DNA Computing", Lecture Notes in Computer Science, 2007, vol. 4848, pp. 152-160.

Stojanovic, M. et al., "Deoxyribozyme-Based Logic Gates", Journal of the American Chemical Society, Mar. 2002, vol. 124, No. 14, pp. 3555-3561 <DOI:10.1021/ja016756v>.

St-Pierre, F. et al., "One-Step Cloning and Chromosomal Integration of DNA", ACS Synthetic Biology, May 2013, vol. 2, No. 9, pp. 537-541 <DOI:10.1021/sb400021j>.

Tanaka, F. et al., "Design of nucleic acid sequences for DNA computing based on a thermodynamic approach", Nucleic Acids Research, Jan. 2005, vol. 33, No. 3, pp. 903-911 <DOI:10.1093/nar/gki235>.

Vaziri, H. et al., "Evidence for a Mitotic Clock in Human Hematopoietic Stem-Cells—Loss of Telomeric DNA with Age", Proceedings of the National Academy of Sciences of the United States of America, Oct. 1994, vol. 91, No. 21, pp. 9857-9860 <DOI:10.1073/pnas.91.21.9857>.

Wang, F. et al., "Robust measurement of telomere length in single cells", Proceedings of the National Academy of Sciences of the United States of America, May 2013, vol. 110, No. 21, pp. E1906-E1912 <DOI:10.1073/pnas.1306639110>.

Willeit, P. et al., "Telomere Length and Risk of Incident Cancer and Cancer Mortality", JAMA, Jul. 2010, vol. 304, No. 1, pp. 69-75 <DOI:10.1001/jama.2010.897>.

Wu, M. et al., "Engineering of regulated stochastic cell fate determination", Proceedings of the National Academy of Sciences of the United States of America, Jun. 2013, vol. 110, No. 26, pp. 10610-10615 <DOI:10.1073/pnas.1305423110>.

Xie, Z. et al., "Multi-Input RNAi-Based Logic Circuit for Identification of Specific Cancer Cells", Science, Sep. 2011, vol. 333, No. 6047, pp. 1307-1311 <DOI:10.1126/science.1205527>.

Xiong, F. et al., "Padlock probe-mediated qRT-PCR for DNA computing answer determination", Natural Computing, Jun. 2011 (available online Nov. 2010), vol. 10, No. 2, pp. 947-959 <DOI:10.1007/s11047-010-9227-8>.

Xiong, F. et al., "Solving the fully-connected 15-city TSP using probabilistic DNA computing", Integrative Biology, Mar. 2009 (available online Feb. 2009), vol. 1, No. 3, pp. 275-280 <DOI:doi.org/10.1039/b821735c>.

Zhu, H. et al., "Healthy aging and disease: role for telomere biology?", Clinical Science, May 2011, vol. 120, No. 10, pp. 427-440 <DOI:10.1042/CS20100385>.

\* cited by examiner

PROBES AND METHODS FOR MEASURING TANDEM REPEATS

CROSS REFERENCE TO RELATED APPLICATIONS

This application is a Continuation of U.S. patent application Ser. No. 16/886,205, filed May 28, 2020 (published as US 20200291475), which is a Continuation of U.S. patent application Ser. No. 16/089,887, filed Sep. 28, 2018 (issued as U.S. Pat. No. 10,718,017), which is the U.S. National Stage of International Patent Application No. PCT/US2017/025389, filed Mar. 31, 2017, which claims priority to and the benefit of U.S. Provisional Application No. 62/316,538 filed Mar. 31, 2016, the contents of each of which are hereby incorporated by reference in their entireties.

REFERENCE TO SEQUENCE LISTING SUBMITTED ELECTRONICALLY

The official copy of the sequence listing is submitted electronically via EFS-Web as an ASCII-formatted sequence listing with a file named "11157_016USCON_SeqList_updated.txt" created on Apr. 26, 2021 and having a size of 3,191 bytes and is filed concurrently with the specification. The sequence listing contained in this ASCII-formatted document is part of the specification and is herein incorporated by reference in its entirety.

TECHNICAL FIELD

The present disclosure relates to nucleic acid probes and methods for detection of tandem repeats, such as telomeres and sub-telomeres, and methods of using such probes for determining the length of tandem repeats.

BACKGROUND

Tandem repeats occur in DNA when a pattern of one or more nucleotides is repeated and the repetitions are directly adjacent to each other. Detection of tandem repeats helps determine an individual's inherited traits and can also determine the individual's parentage. However, detection of tandem repeats can go beyond these uses. In particular, telomeres and sub-telomeres are tandem repeats. Knowing the length of telomeres can have clinical diagnostic applications.

The nuclear DNA in the human genome is partitioned into 23 separate pairs of chromosomes. Each pair of sister chromatids is attached by a protein complex at a central region of the chromosome known as the centromere. The distal regions of each chromatid are known as telomeres, which contain long stretches of repetitive nucleotide sequences at the termini of these linear DNA strands, are found in most eukaryotic organisms. For vertebrates, the repeated nucleotide sequence in telomeres is TTAGGG, the total length of which can be many kilobases (kb) long in humans (Moyzis et al., 1988).

The DNA polymerase protein complex responsible for DNA replication can only add nucleotides to an existing DNA or RNA strand that is paired with the template strand, and can only extend the new DNA sequence in the 5' to 3' direction. Thus, replication begins at the 5' end a short nucleic acid fragment primer that must be bound to the template DNA strand. As a consequence, the polymerase is not able to replicate the sequences at the ends of the chromatid fibers. Consequently, chromatids become shorter with each successive cell division and the information in the telomeric region is lost. Normal human somatic cells such as fibroblasts, endothelia, and epithelial cells, telomeres have been shown to become shorter by 8-33 repeat sequences (50-200 bp) with each cell division event (Blackburn, 2000, 2001). The cumulative loss of telomeric DNA with successive cell divisions is believed to limit the number of times that a cell can divide. In human fibroblasts, this limit occurs after the cell population has doubled 50-100 times. The cells then remain in a quiescent but viable state for several months (Vaziri et al., 1994). Consequently, cell division stops before vital genetic information is lost from the chromosome.

Some types of white blood cells, certain stem cells such as embryonic stem cells, and germ cells can express an active form of telomerase that is capable of adding the repetitive nucleotide sequences to the ends of the DNA (Hiyama and Hiyama, 2007). This enzyme can "reset" the cell to an embryonic state, which restores its ability to undergo cell division. Developing the ability to reactivate telomerase in quiescent somatic cells that restores their ability to undergo cell division has important implications for the restoration of damaged tissues. However, the activation of telomerase is known to contribute significantly to the ability of malignant cells to proliferate and become immortalized.

Conversely, many aging-related diseases are linked to shortened telomeres (Zhu et al., 2011). Eukaryotic telomere ends contain a 3' single stranded DNA overhang that forms a T-loop (telomeric loop). This loop is stabilized by a triple-stranded DNA structure known as a D-loop (displacement loop) that is also bound to several proteins that forms an end cap. When telomeres become too short there is an increased potential for damage to the end cap that can cause the cell to stop growing or go into senescence (cellular old age). Chromosomal fusions can also result when telomeres are uncapped, which cannot be repaired in somatic cells, and can induce apoptosis (cell death). Such increases in the number of cells undergoing senescence and apoptosis ultimately results in age-related organ deterioration (Aubert and Lansdorp, 2008).

It is clear that the ability to calculate the length of telomeres accurately and in a timely manner will be an important tool for the early diagnosis of cancer and for age-related illness, and also has valuable application in the development of stem cell technologies. To identify precancerous cells, the approach must be able to compute telomere lengths from the DNA of a single cell, and preferably be able to make the computation for each individual chromosome. To be practical, the computational approach requires high-throughput capability for the analysis of large numbers of samples.

Currently, none of the methods available are capable of directly measuring the length of telomeres in single cells without PCR amplification, let alone individual chromosomes (Wang et al., 2013). In addition, the errors in the existing calculations are so large as to limit their usefulness for practical diagnostic applications. Methods currently employed include terminal restriction fragment (TRF) Southern blots, fluorescent in situ hybridization methods known as Q-FISH and F-FISH, as well as PCR and quantitative real-time PCR assays.

1. TRF Computations

Telomere length is most commonly calculated by TRF analysis that provides the average length of fragments generated by complete digestion of genomic DNA with a restriction enzyme that does not cleave nucleic acids composed entirely of tandem arrays of the specific telomeric repeat sequence of interest (Kimura et al., 2010). This approach is only capable of calculating the mean telomere length of all chromosomes and requires large numbers (>105) of cells. In addition, TRF analysis can be confounded by the presence of interstitial telomeric sequences. The answer is calculated by separating the digested DNA fragments by electrophoresis, followed by a Southern blot where the DNA is hybridized to a radio-labelled telomeric probe. The telomeric DNA is then visualized by autoradiography and the answer is calculated from densitometric scans that estimate the amount of DNA in each band.

It is noteworthy that the use of densitometric scans of Southern blots in TRF has similarities to the DNA computing answer determination approach that we initially used to solve the asymmetric fully-connected 15-city traveling salesman problem (Xiong et al., 2009). Consequently, we are very familiar with the limitations in accuracy inherent in this time-consuming approach. Difficulties inherent in the electrophoretic migration of short DNA fragments also limit the ability of TRF to compute the length of short telomeres that are crucial for aging studies.

2. FISH Methods

The FISH techniques to calculate the telomere length can be accomplished with <30 cells and enables the length of individual chromosome arms to be determined. In these approaches, fluorescent protein nucleic acid (PNA) probes are hybridized to the DNA in a group of cells (Lansdorp et al., 1996; Martens et al., 2000; Perner et al., 2003). Fluorescence intensity, which is proportional to telomere length, is then measured using flow cytometry that examines one cell at a time. This time-intensive measurement severely limits the amount of samples that can be examined. The Q-FISH approach requires the use of metaphase cells, which forces the use of cultured cells and severely limits the number of cells available for the calculation (Ferlicot et al., 2003). This requirement also eliminates the ability of the method to determine telomere lengths of many of the most valuable cell types for diagnostic purposes such as post-mitotic, differentiated, and senescent cells.

The answer read-out with FISH is in arbitrary integrated fluorescence intensity units that are difficult to quantitate. Thus, to compute absolute values of telomere length, external calibration using plasmids with cloned telomere repeats of defined length, or cell lines that maintain a defined and known telomere length distribution are required for calibration. The fact that the calculation is based on hybridization imposes a minimum telomere length threshold below which the length cannot be calculated. In some cell lines, the standard deviation of the fluorescent intensity is higher than the entire range of telomere lengths (~8 kb) (O'Sullivan et al., 2002).

The IQ-FISH method is an adaptation of Q-FISH that measures fluorescence intensity of probes hybridized to telomeres in individual interphase cells using fluorescence-activated cell sorting (FACS) technology (Narath et al., 2005). Following hybridization with fluorescent PNA probes specific to telomeres, the DNA is counterstained to normalize DNA content. The IQ-FISH approach requires accurate measurements of relatively weak fluorescence signals. Marked day-to-day variations in instrument calibration, and in hybridization efficiencies due to the fixatives that are required for cell preparation limit the accuracy and reproducibility of telomere length computations to a range that is greater than the length differences of 2-10 kb typically found in human cells.

3. PCR Approaches

The polymerase-chain reaction will amplify the number of copies of DNA strands along a chosen section of the parent strands defined by the two unique DNA primers bound at each end. Unfortunately, the repeating nature of the short telomeric DNA sequence $(TTAGGG)_n$ enables PCR primers to hybridize in myriad combinations staggered along the length of the telomere. As a result, heterogeneous amplification reactions occur simultaneously that make the computation of telomere length extremely difficult.

The PCR-based approach known as STELA (single telomere elongation length analysis) has been developed (Baird et al., 2003) that has higher resolution than other currently available approaches. However, since the length of DNA amplified by PCR is limited to ~25 kb, longer telomeres cannot be amplified and the method is biased in favor of shorter telomeres. STELA also requires a known sub-telomeric primer binding site, which appears to be species-specific and difficult to obtain. This approach involves the ligation of an oligonucleotide to the 5' end of the telomere that may end in any of the six nucleotides within the telomeric repeat sequence. To facilitate ligation, six telomerettes must be made and used, each carrying one of the six possible frames of a telomeric repeat at the 3' end.

SUMMARY OF THE DISCLOSURE

The disclosure is directed to nucleic acid probes and method of detecting and analyzing a region of tandem repeats in DNA. In certain embodiments, the nucleic acid probe comprises a 5' hybridization arm, a reverse PCR primer-binding region, a forward PCR primer region, a minor grove binding (MGB) probe region, and a 3' hybridization arm. The 5' hybridization arm and 3' hybridization arm are complementary adjacent regions in the region of tandem repeats in DNA. In certain embodiments, the 5' hybridization arm and 3' hybridization arm become ligated when they are hybridized to adjacent regions in the region of tandem repeats in DNA, such that the nucleic acid probe can hybridize to the target DNA. In certain embodiments, elements of the nucleic acid probe ordered second and fourth in the 5' to 3' direction each form a stem-loop structure. In certain embodiments, the ΔG of each sequence of second and fourth element is about 10.54 kcal/mol at 37° C. In some embodiments, the nucleic acid probe comprises these elements in the above listed order from 5' to 3'. Thus, the reverse PCR primer-binding region and the MGB probe region form each form a stem-loop structure. An exemplary sequence for the reverse PCR primer-binding region comprises CCGCGCTAGACTAAGCGCTC (SEQ ID NO:3). The MGB probe region may be for a TaqMan®-MGB probe, thus an exemplary sequence for the MGB probe region comprises CAACTAGATGCCGCC (SEQ ID NO:8). The forward primer region may comprise CAGTGACTCAGCAGCTACCCG (SEQ ID NO:5).

In embodiments where the nucleic acid probe is used for detecting telomeres, the region of the telomere to which the 5' hybridization arm and 3' hybridization arm is typically complementary and comprises repeats of TTAGGG. Thus, in this embodiment the 5' hybridization arm and the 3' hybridization arm comprise repeats of CCCTAA. In certain embodiments, the region of the telomere to which the 5' hybridization arm and 3' hybridization arm is complementary comprises at least six repeats of TTAGGG. Accordingly, the sequences of 5' hybridization arm and 3' hybridization arm together comprise at least six repeats of CCCTAA. For example, the 5' hybridization arm may comprise AACCCTAACCCTAACC (SEQ ID NO:1) while the 3' hybridization arm may comprise CCTAACCCTAACCCT (SEQ ID NO:2).

The disclosure is also directed to methods of determining the length of a region of tandem repeats in a DNA sample. The DNA sample may be selected from the group consisting of: isolated coding sequences of a gene, isolated non-coding sequences of a gene, and an isolated intergenic region. The method comprises first hybridizing the nucleic acid probe to the DNA sample. A ligase is then added to ligate the 5' hybridization arm and the 3' hybridization arm when the 5' and 3' hybridization arms are hybridized to adjacent regions on the DNA sample in order to form a circularized DNA with a nucleic acid probe. Any nucleic acid probe that could not be ligated or formed into circularized DNA is digested by an exonuclease. The length of the region of tandem repeats in the DNA sample is determined from the number of circularized DNA formed.

For example, to determine the length of telomeres of a subject's genome, the steps for forming the circularized DNA generally comprise the following steps of: extracting the subject's genomic DNA from a biological sample to produce a DNA template source; providing a reaction mixture, the reacting mixture comprising the DNA template source and nucleic acid probe; hybridizing the nucleic acid probe to the DNA template source; adding to the reaction mixture a ligase to ligate together the 5' hybridization arm and 3' hybridization arm of the nucleic acid probe to form a circularized DNA after the 5' hybridization arm and the 3' hybridization arm of the nucleic acid probe are hybridized to adjacent regions on the genomic DNA; and adding to the reaction mixture exonucleases after the ligase is added to the reaction mixture to digest unligated nucleic acid probes to produce a quantification sample. The exonucleases may comprise least one of Exo I and Exo III.

In certain embodiments, the number of circularized DNA in the quantification sample is determined using a qRT PCR assay. Quantifying the amount of circular DNA comprises conducting a first qRT-PCR reaction with a first qRT-PCR reaction mixture to calculate a Ct value for the first qRT-PCR reaction, wherein the first reaction mixture the quantification sample, a first forward primer, a first reverse primer, and a fluorescent probe. The quantification sample is linear complement to circular DNA Ω probe extended using the first reverse primer, which binds to the reverse PCR primer-binding region. Thus, the quantification sample also comprises a forward PCR primer-binding region (complementary to the forward primer region on the Ω probe) and the MGB binding region (complementary to the MGB probe region on the Ω probe). The first reverse primer binds to the sequence that corresponds to the reverse PCR primer-binding region on the Ω probe. The fluorescent probe comprises a fluorophore at the 5' end and a nonfluorescent quencher (NFQ) at the 3' end and binds to the MGB probe region. The fluorophore may be selected from the group consisting of: 6FAM, VIC, NED, Cy5, and Cy3.

Quantifying the amount of circular nucleic acid probes is preferably based on the Ct value of the first qRT-PCR reaction. In some embodiments, the fluorescent MGB probe comprises an oligonucleotide sequence of CAACTAGATGCCGCCC (SEQ ID NO:8). Preferably, the fluorescent probe comprises 6FAM at the 5' end and a NFQ at the 3' end, where the NFQ is coupled with a MGB. In some embodiments, the first forward primer comprises CAGTGACTCAGCAGCTACCCG (SEQ ID NO:5). In some embodiments, the first reverse primer comprises GAGCGCTTAGTCTAGCGCG (SEQ ID NO:6).

To determine the length of telomeres of a subject's genome, the amount of circularized DNA is divided by the number of copies of genomic DNA in the quantification sample. Accordingly, the method comprises conducting a second qRT-PCR reaction with a second qRT-PCR reaction mixture to calculate a Ct value for the second qRT-PCR reaction, wherein the second qRT-PCR reaction mixture comprises the DNA template source, a second forward primer, a second reverse primer, and the fluorescent probe, wherein the second forward primer and the second reverse primer flank a single-copy housekeeping gene of the genomic DNA, and determining the amount of the genomic DNA in the DNA template source based on the Ct value of the second qRT-PCR reaction. The number of copies of the genomic DNA in the DNA template source is calculated from the amount of the genomic DNA, and the length of telomeres of the subject's genome is calculated by dividing the amount of circularized DNA with the number of copies of genomic DNA. Where the single-copy housekeeping gene is 36B4, the second forward primer and the second reverse primer may respectively be CAGCAAGTGGGAAGGTGTAATCC (SEQ ID NO:9) and CCCATTCTATCATCAACGGGTACAA (SEQ ID NO:10).

The disclosure also provides kits for quantifying the total length of telomeres in a sample. The kit comprises the nucleic acid probe of the disclosure, a first forward primer, a first reverse primer, and a MGB fluorescent probe. The first forward primer comprises CAGTGACTCAGCAGCTACCCG (SEQ ID NO:5). The first reverse primer comprises GAGCGCTTAGTCTAGCGCG (SEQ ID NO:6). The MGB fluorescent probe CAACTAGATGCCGCCC (SEQ ID NO:8), and it has a fluorophore at the 5' end and an MGB nonfluorescent quencher (MGBNFQ) at the 3' end.

In some embodiments, the kits are designed to quantify the total length of telomeres per copy of genomic DNA. Such kits further comprise a second forward primer, a second reverse primer, and a fluores cent probe. The second forward primer and the second reverse primer flank a single-copy housekeeping gene of the genomic DNA. In some implementations, the housekeeping gene is 36B4. Thus, the second forward primer may comprise CAGCAAGTGGGAAGGTGTAATCC (SEQ ID NO:9), and the second reverse primer may comprise CCCATTCTATCATCAACGGGTACAA (SEQ ID NO:10).

DETAILED DESCRIPTION

Figure 1:
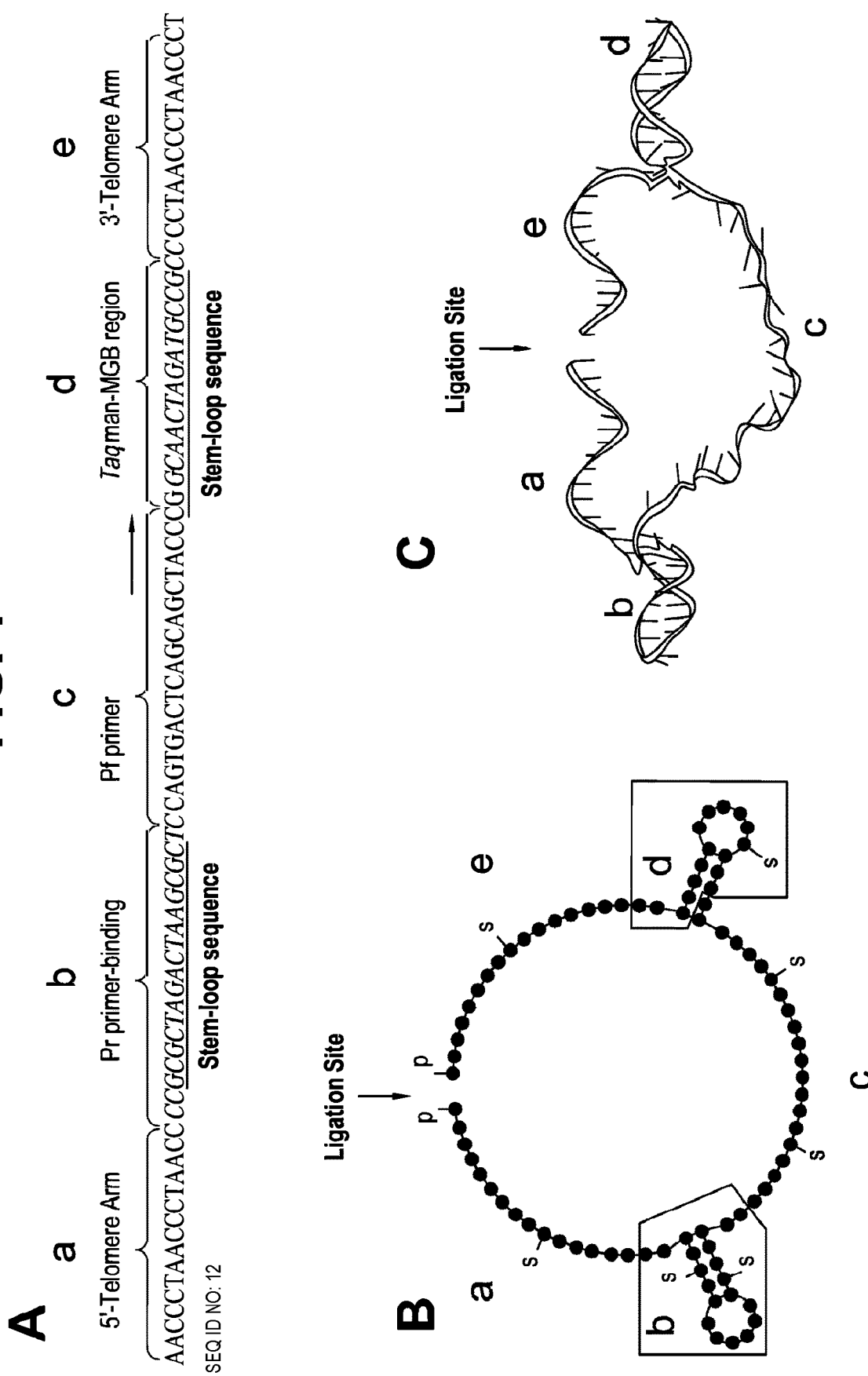
FIG. 1 depicts a schematic of the nucleic acid probe for calculating telomere length. Such a nucleic acid probe comprises five regions: a 5' hybridization arm (a), a reverse PCR primer-binding region (b), a forward primer region (c), a TaqMan®-MGB probe region (d), and a 3' hybridization arm (e). Panel A lists the DNA sequence for an exemplary nucleic acid probe. The underlined sequences indicate the bases that form stem-loop structures. Panel B depicts a two-dimensional representation of the nucleic acid probe showing the stem loop structures. Panel C depicts a three-dimensional molecular model of the nucleic acid probe.

Detailed aspects and applications of the disclosure are described below in the drawings and detailed description of the disclosure. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that the present disclosure may be practiced without these specific details. It should be noted that there are many different and alternative configurations, devices and technologies to which the disclosed disclosures may be applied. The full scope of the disclosures is not limited to the examples that are described below.

The singular forms "a," "an," and "the" include plural referents unless the context clearly dictates otherwise. Thus, for example, reference to "a step" includes reference to one or more of such steps.

As used herein, the term "circular DNA" and "circularized DNA" refer to a nucleic acid probe, also called an Ω probe, after it properly hybridized to the DNA template so that a ligase ligates the 5' end and 3' end of the nucleic acid probe.

This disclosure is directed to calculating the length of region of tandem repeats using specifically-designed nucleic acid probes and the nucleic acid probes themselves. These nucleic acid probes are also designed to provide an answer read out using qRT-PCR in less than 30 minutes (Xiong and Frasch, 2011). Thus, the disclosure provides methods and techniques of rapidly determining the length of a region of tandem repeats. The tandem repeats may be within isolated coding sequences of a gene, isolated non-coding sequences of a gene, and an isolated intergenic region.

In some embodiments, the nucleic acid probes calculate the length of telomeres in a cell. In certain embodiments, the cells are of mammalian origin, for example, from humans. In some implementations, the nucleic acid probes are capable of calculating telomere length from each chromosome separately. In other implementations, the nucleic acid probes are capable of calculating telomere length from each end of the chromosome.

1. The Nucleic Acid Probe, Designated Omega (Ω) Probe

The Ω probe comprises a 5' hybridization arm, a reverse PCR primer-binding region, a forward PCR primer region, a MGB probe region, and a 3' hybridization arm (FIG. 1). The 5' hybridization arm is at the 5' end of the Ω probe while the 3' hybridization arm is at the 3' end of the Ω probe. The MGB probe region may be, for example, a TaqMan®-MGB probe. In certain embodiments, the order of the elements of the Ω probe from 5' to 3' is the 5' hybridization arm, the reverse PCR primer-binding region, the forward PCR primer region, the MGB probe region, and the 3' hybridization arm.

To promote the hybridization of the Ω probe for ligation, the design of the reverse PCR primer-binding region and the MGB probe region comprise sequences that form stem-loop structures. In certain embodiments, the sequences of reverse primer binding region and the MGB probe region form stem-loop structures (see FIG. 1). Preferably, the sequence for the reverse primer binding region and the MGB probe region comprise sequences that form stem-loop structures has a ΔG of −10.54 kcal/mol at 37° C. based on M-folding analysis prediction. For example, the sequence for the MGB probe region comprises CAACTAGATGCCGCCC (SEQ ID NO:8). As another example, the sequence for the reverse PCR primer-binding region comprises CCGCGCTA-GACTAAGCGCTC (SEQ ID NO:3). In this embodiment, the forward PCR primer region may comprise CAGTGACTCAGCAGCTACCCG (SEQ ID NO:5).

The 5' hybridization arm and the 3' hybridization arm are complements to the region of tandem repeats. Specifically, the region of tandem repeats to which the 5' hybridization arm is complementary is adjacent to the region of tandem repeats to which the 3' hybridization arm is complementary. Thus upon hybridization with the DNA template and if there is an exact base pair match of the double-stranded DNA at the ligation site, the 5'- and 3'-ends of the Ω probe become juxtaposed and can be ligated to form circular DNA.

The specific sequence of the 5' hybridization arm and the 3' hybridization arm should comprise multiple repeats of the sequence repeated in the region of tandem repeats. In the case of a Ω probe for detecting the length of telomeres, the 5' hybridization arm and 3' hybridization arm are comprises multiple repeats of TTAGGG. Thus the 5' hybridization arm and 3' hybridization arm comprise repeats of CCCTAA. As the repeated sequence of the telomere and sub-telomere differ only by one nucleotide, in more certain embodiments of Ω probes for determining the length of telomeres, the 5' and 3' hybridization arms are designed so that the point of ligation of the hybridization arms occurred at the base that varies in the sub-telomere region. Accordingly, in some certain embodiments, the 5' hybridization arm comprises AACCCTAACCCTAACC (SEQ ID NO:1) and/or the 3' hybridization arm comprises CCTAACCCTAACCCT (SEQ ID NO:2).

2. Methods of Calculating the Length of the Region of Tandem Repeats

Figure 2:
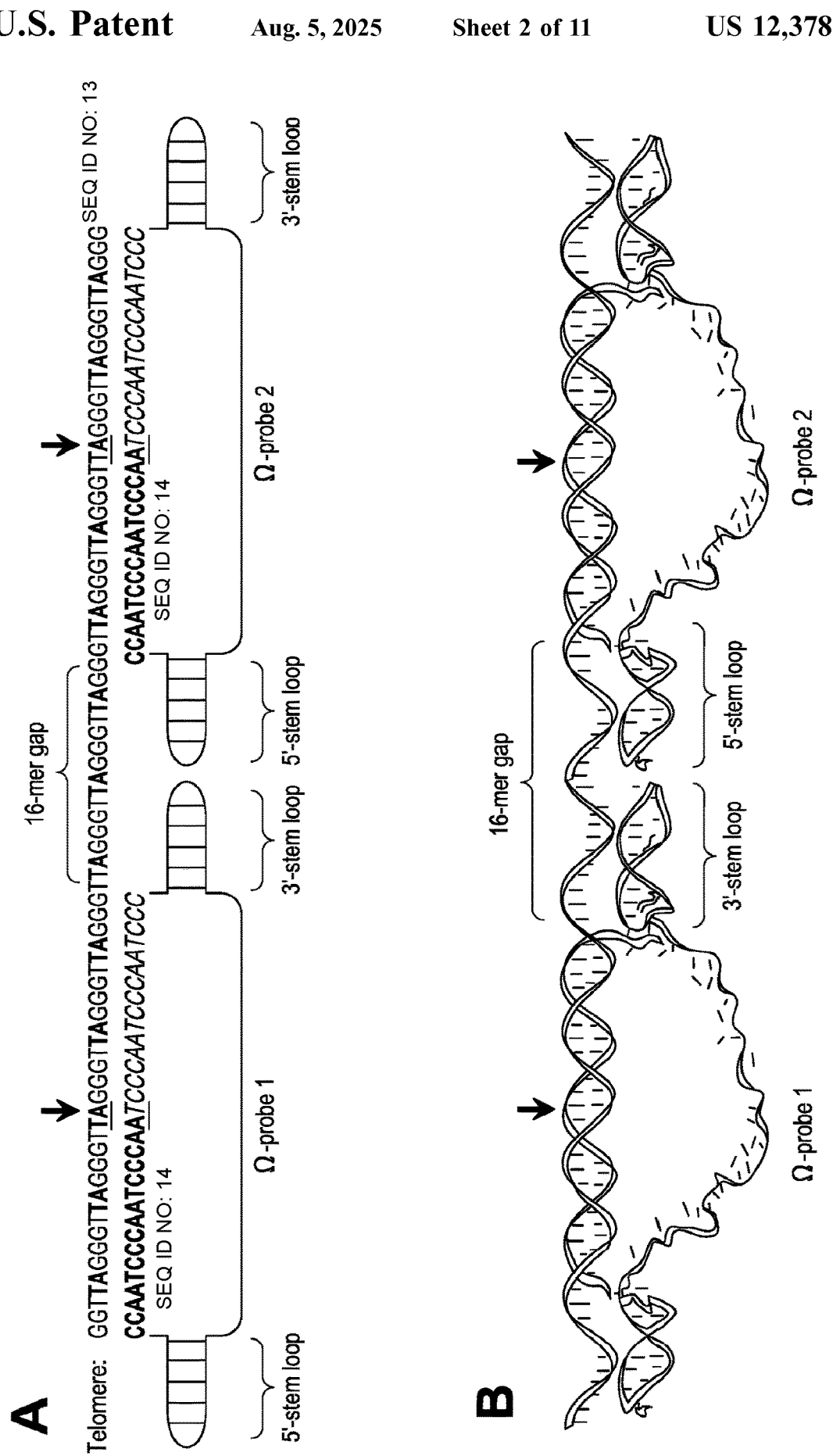
FIG. 2 depicts the hybridization of two nucleic acid probes, designated Ω-probe 1 and Ω-probe 2, to adjacent sequences of a telomeric DNA strand. The distance between the two Ω-probes is 16-nucleotide gap. The bold arrow points to the ligation/circularization site. Addition of ligase causes each nucleic acid probe to become circularized. Linearization and circularization of the Ω-probe requires exact base pair match. The number of copies of the circularized nucleic acid probe is then determined by qRT-PCR to compute telomere length. The requirement that ligation can occur only if there is an exact base-pair match at the ligation site minimizes the probability of circularization of nucleic acid probes that may have hybridized to stretches of the sub-telomere that contain a TXGGGT repeat where x is mostly G. Panel A depicts the two-dimensional representation of two nucleic acid probes hybridized to adjacent sequences of telomeric DNA. Panel B depicts a three-dimensional molecular model of Panel A.
Figure 3:
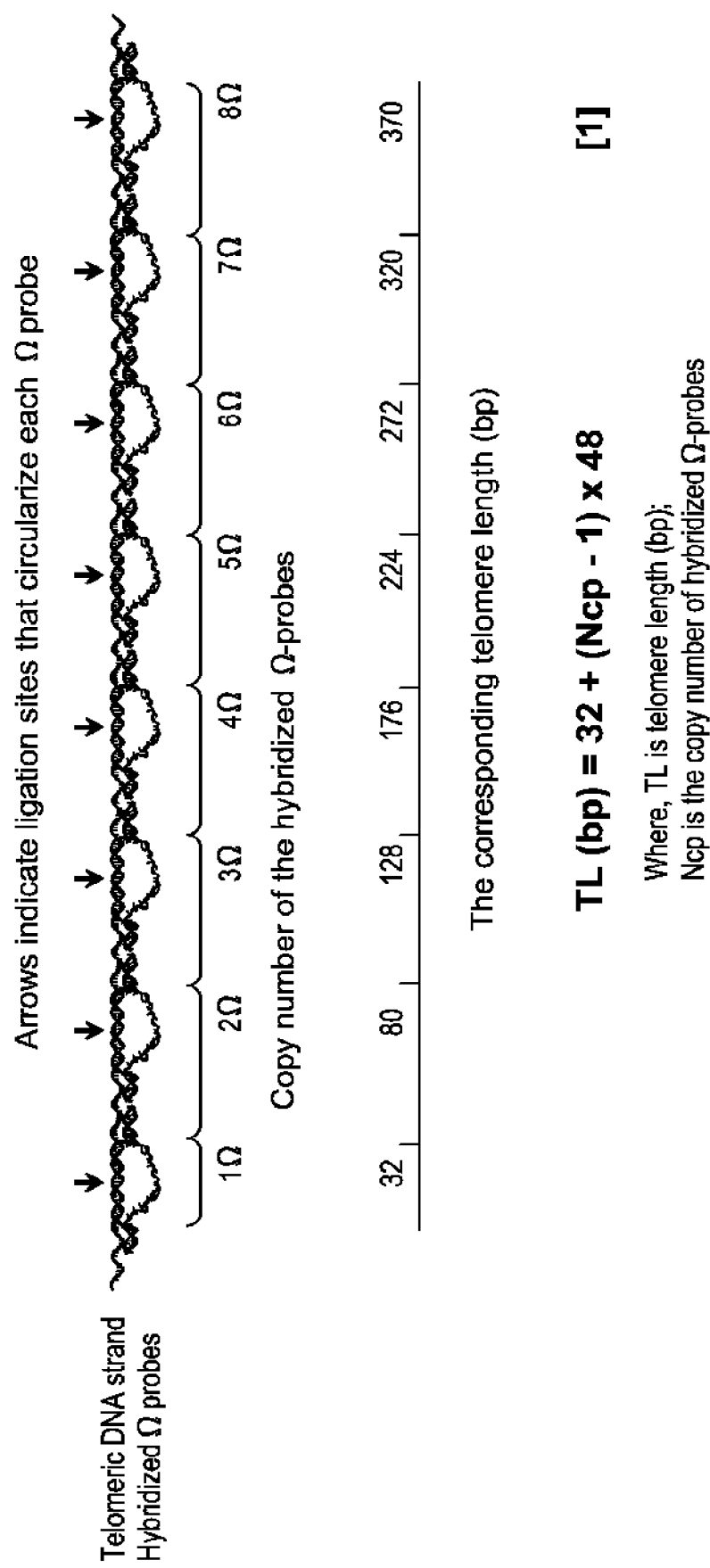
FIG. 3 depicts the correlation between the number of nucleic acid probes, designated probe, that become circularized upon hybridization to telomeres and subsequent ligation with the length of the telomere. Telomere length is then calculated from the number of circularized nucleic acid probes by Equation 1 where TL is telomere length in base pairs, and NCP is the copy number of hybridized nucleic acid probes.

The method of calculating the length of the region of tandem repeats using the Ω probe comprises hybridizing the Ω probe to the target DNA, ligating the 5'- and 3'-ends of the Ω probe to form a circularized DNA, digesting unligated Ω probes with exonucleases, and quantifying the number of circularized DNA (FIGS. 2 and 3). The specific ligase and exonucleases that may be used are evident to a person having ordinary skill in the art. For example, the exonucleases may be exonuclease I (ExoI), exonuclease III (ExoIII), or a combination of both (ExoI/III). The target DNA serves as the DNA template source and should be from an extract or isolated DNA sample. For example, for determining the length of telomeres in subject's genome, the target DNA is the subject's genome DNA extracted from a biological sample. In some embodiments, the target DNA may be isolated genomic DNA. In other embodiments, the Ω probe assay components are directly added to the cell lysate for hybridization/circularization, so the target DNA is not extracted or purified.

In some embodiments, hybridizing the Ω probe to the target DNA comprises first denaturing the target DNA, for example incubating the target DNA in 94° C. for 2.5 minutes followed by quick cooling, such as on ice. After cooling, the Ω probes are added to the denatured target DNA for hybridization. In certain embodiments, hybridization takes place with a slow annealing process comprising incubation at 55° C. for three hours. In embodiments in which hybridizing the Ω probes to the target DNA takes place uses a thermal cycler, the thermal cycler may be programmed to heat the sample to 94° C. and remain at that temperature for 2.5 minutes followed by ramp cool to 55° C. over a period of 45 minutes at a cooling rate of 1° C. min$^{-1}$. In some embodiments, the process is followed by incubation at 16° C. or 55° C. to for ligating to form circularized DNA and digestion of unligated Ω probes.

In certain embodiments, the step of quantifying the number of circularized DNA involves using a MGB probe, such as a TaqMan®-MGB probe, to detect the circularized DNA. In some embodiments, the MGB probe comprises a fluorophore at the 5' end and a non-fluorescent quencher (NFQ) at the 3' end, where the NFQ is coupled to the MGB molecule to form an MGBNFQ complex at the 3' end of the TaqMan®-MGB probe. In embodiments where the amount of circularized DNA is determined using a TaqMan®-MGB probe, the step of quantifying the number of circularized DNA may use a qRT-PCR assay to quantify the number of circularized DNA according to the signal generated by the TaqMan®-MGB probe. The methods of the qRT-PCR are standard in the field. Examples 2 and 3 provide some preferred conditions for the qRT-PCR. For example, for every 1 ng of genomic DNA, at least 0.1-0.2 nmol of Ω probe should be added. In other implementations, at least 3 nM, at least 3.5 nM at least 4 nM, at least 4.5 nM, at least 5 nM, at least 5.5 nM, at least 6 nM, at least 6.5 nM, at least 7 nM, at least 7.5 nM, or at least 8 nM Ω probe should be added for every pg of genomic DNA. The melting temperature for determining telomere length may be less than 60° C. but above 55° C., for example 58° C. Preferably the melting temperature is at or above 60° C., for example between 60° C. and 62° C. and between 62° C. and 65° C.

The number of Ω probes that hybridize to a target DNA and can be ligated to form circularized DNA corresponds to the length of the tandem region on the target DNA (see FIG. 3 for an example). For determining the length of telomeres, one Ω probe that hybridizes to the telomere and can be ligated to form circularized DNA corresponds to a telomere length of 32 bp, while two Ω probes correspond to 80 bp, three Ω probes correspond to 128 bp, (FIG. 3) and so forth for increasing numbers of Ω probes, according to Equation 1:

$$TL = 32 + (N_{cp} - 1) \times 48, \text{ where} \qquad (Eq. 1)$$

TL is the length of telomeres in base pairs (bp), and Ncp is the number circularized Ω probes. This method provides a direct measurement of telomere length that is not relative. This can be expressed as an average telomere length for all chromosomes in a cell, or as the length of individual chromosome arms (p- and q-arms) from a cell.

Figure 4:
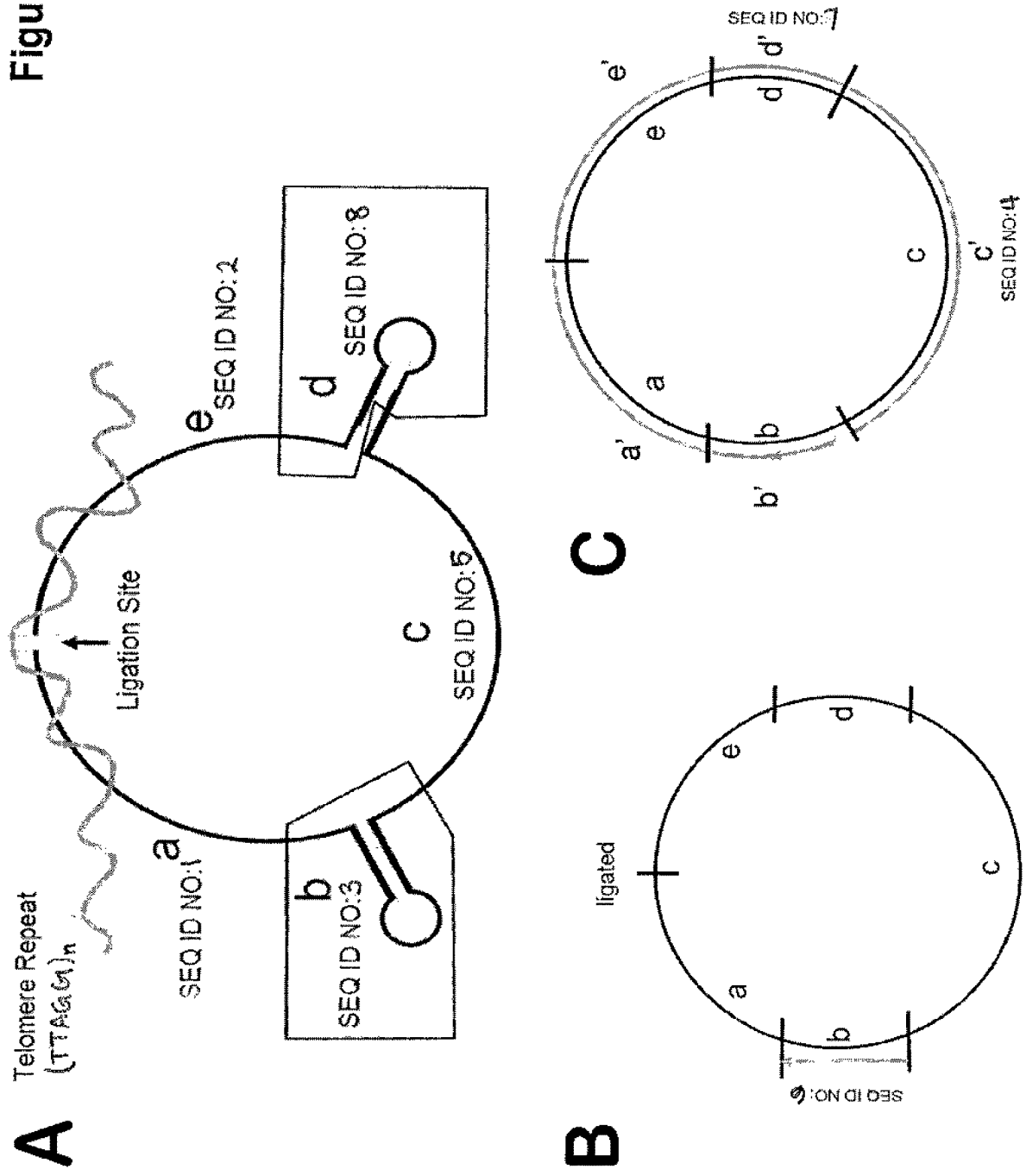
FIG. 4 depicts the steps that quantitate the number of ligated/circularized Ω probes using qRT-PCR. The parts of the Ω probe are labeled as in FIG. 1. Panel A show a Ω Probe that has hybridized to the telomere repeat sequence, which is ligated and circularized only if there is an exact base pair match at the site of ligation. Panel B shows that after exonuclease has removed linear DNA strands (in particular unligated Ω probe), a reverse primer (SEQ ID NO:6) that is complimentary to the reverse PCR primer-binding region (b) is added to create the complimentary linear strand to the circularized Ω Probe. Panel C shows the first PCR creates a linear DNA strand that contains a TaqMan®-MGB binding region (SEQ ID NO:7). Panels D and E show that the first forward primer (SEQ ID NO:5) creates the complimentary strand from the linear DNA strand formed in Panel C. Panels F and G shows that during qRT-PCR, the fluorescence increases as the TaqMan-MGB probe (SEQ ID NO:8) that has hybridized to the TaqMan®-MGB binding region (SEQ ID NO:7) is displaced and degraded upon formation of the complimentary DNA strand.
Figure 4:
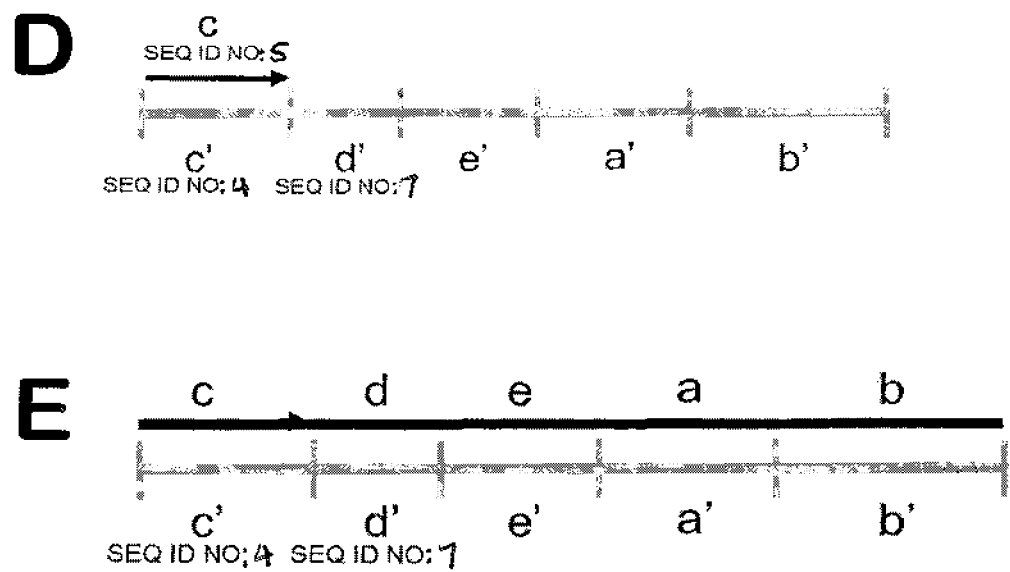
Figure 4:
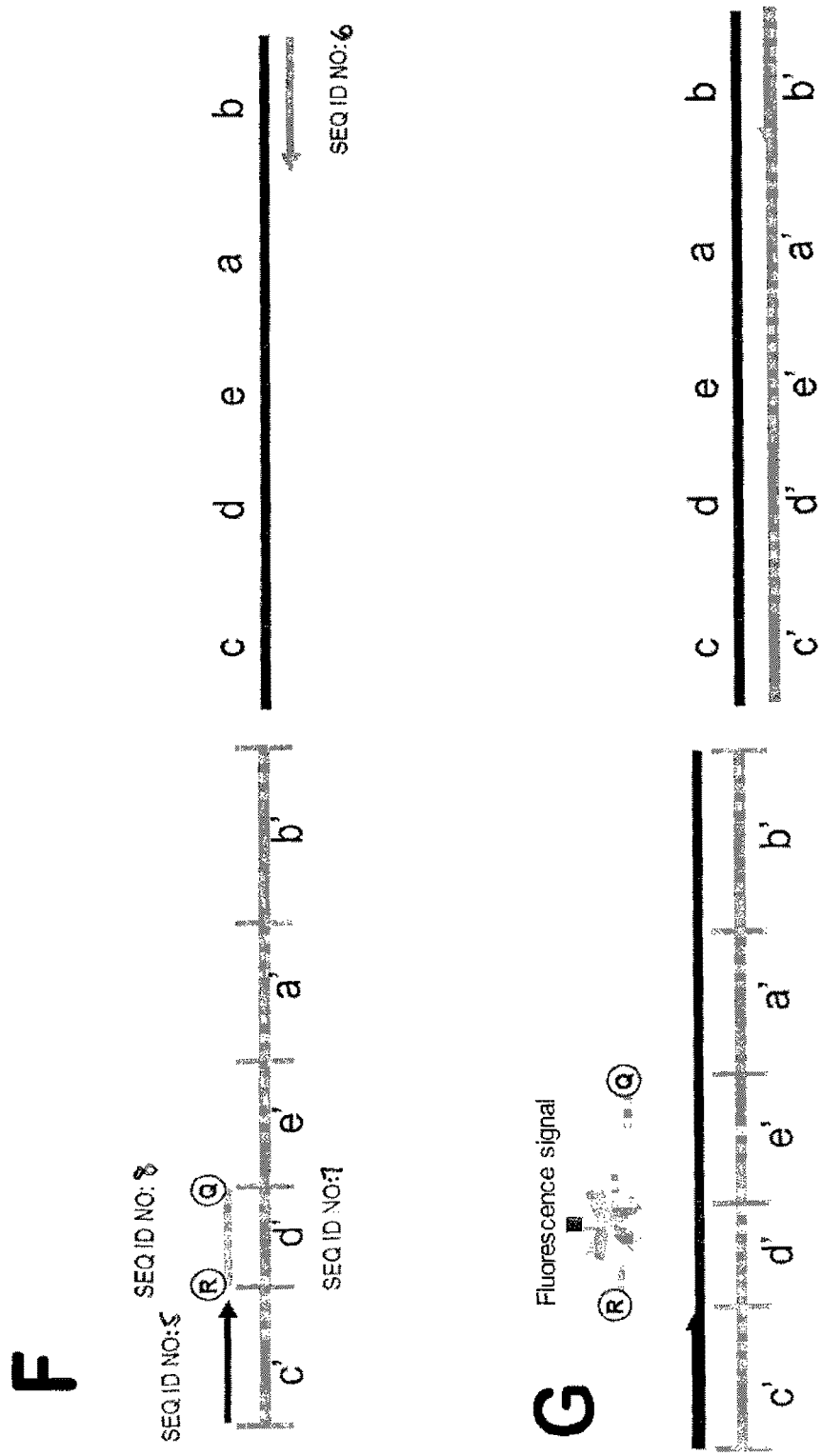

While quantifying the number of circularized DNA may be accomplished by a variety of quantification methods well established in the art, the certain embodiments quantify the number of circularized DNA using a quantitative real-time PCR (qRT PCR) assay (FIG. 4). For example, such embodiments comprise conducting a first qRT-PCR reaction with a first reaction mixture to calculate a Ct value for the first qRT-PCR reaction involving the circularized DNA Ω probes and determining the amount of the circularized DNA Ω probes based on the Ct value of the first qRT-PCR. The reaction mixture for the first qRT-PCR comprises a quantification sample, a first forward primer, a first reverse primer, and a MGB fluorescent probe (for example a TaqMan®-MGB probe).

The quantification sample is the linear complement of the circularized DNA Ω probe, the product of ligation of the Ω probe after hybridization of the Ω probe and the target DNA. The quantification sample is created by extending the circularized DNA Ω probe with the first reverse primer, which binds to the reverse PCR primer-binding region. The quantification sample is produced after the digestion of any unligated Ω probes. In certain embodiments, the order of the newly synthesized DNA strand, from the 5' to 3' direction, is the reverse complement of: the forward primer region, the TaqMan®-MGB probe region, the 3'-telomere hybridization arm, the 5'-telomere hybridization arm, and the reverse PCR primer-binding region.

The first reverse primer binds to the sequence that corresponds to the reverse PCR primer-binding region of the Ω probe to initiate first cycle of PCR reaction. The first forward primer, which corresponds with the sequence of forward primer region of the Ω probe, binds to the forward primer binding region, the reverse complement of the forward primer region. The MGB fluorescent probe comprising a fluorophore at the 5' end and the MGB non-fluorescent quencher (MGBNFQ) at the 3' end binds to the sequence that corresponds to the MGB probe region.

In some embodiments for detecting the length of telomeres, the first forward primer comprises CAGTGACTCAGCAGCTACCCG (SEQ ID NO:5). In some embodiments for detecting the length of telomeres, the first reverse primer comprises GAGCGCT-TAGTCTAGCGCG (SEQ ID NO:6). In some embodiments, the MGB probe comprises an oligonucleotide sequence of CAACTAGATGCCGCC (SEQ ID NO:8). The amount of circularized DNA Ω probes may be determined using techniques established in the prior art for quantifying gene expression using DNA probes. In particular, methods for translating the fluorescence generated by TaqMan®-MGB probes to gene expression and the number of copies of a gene are well established. In the context of the present disclosure, gene expression and the number of copies of a gene corresponds to the amount of circularized DNA Ω probes.

As the DNA template source may comprise multiple copies of the target DNA, the method of calculating the length of the region of tandem repeats further comprises determining the numbers of copies of the target DNA. For example, in methods of calculating the length of telomeres, the method comprises an assay to determine the number of copies of genomic DNA in the DNA template source. In certain embodiment, the assay is a second qRT-PCR reaction involving comprises the DNA template source, a second forward primer, a second reverse primer, and the fluorescent probe, wherein the second forward primer and the second reverse primer flank a single-copy housekeeping gene of the genomic DNA. The single-copy housekeeping gene may be, but is not limited to, 36B4. Thus, exemplary second forward and second reverse primers are CAGCAAGTGG-GAAGGTGTAATCC (SEQ ID NO:9) and CCCATTCTAT-CATCAACGGGTACAA (SEQ ID NO:10), respectively. In one implementation, the second qRT-PCR reaction mixture is 20 µl and comprises 250 nM of 6FAM-TaqMan®-MGB probe. The qRT-PCR reaction condition comprises 58° C. for 30 seconds for both annealing and extension.

The Ct value for the second qRT-PCR reaction may be used to determining the amount of the genomic DNA in the DNA template source. As the average quantity of genomic DNA in a human diploid and haploid cell is 6.6 and 3.3 pg, respectively, the amount of genomic DNA may be used to estimate the number of copies of the genomic DNA. Once the number of copies of the genomic DNA is known, the amount of circularized DNA Ω probe may be divided by that number in order calculated the length of telomeres of the subject's genome. The amount of circularized DNA may be further divided by the number of chromosomes from the biological sample that produced the DNA template source to estimate an average length of telomeres per chromosome.

3. Kits of Determining the Length of the Region of Tandem Repeats

The disclosure also provides for kits for performing the methods of the disclosure. The kit for quantifying the length of a region of tandem repeats in a sample comprises the nucleic acid probe of the disclosure, a first forward primer, a first reverse primer, and a MGB fluorescent probe. The first fluorescent primer is the forward PCR primer of the nucleic acid probe. The first reverse primer binds to the reverse PCR primer-binding region of the nucleic acid probe. The MGB fluorescent probe binds to the MGB probe region of the nucleic acid probe.

In embodiments where the kits quantify the total length of telomeres, the first forward primer may comprise CAGTGACTCAGCAGCTACCCG (SEQ ID NO:5); the first reverse primer may comprise GAGCGCT-TAGTCTAGCGCG (SEQ ID NO:6); and the MGB fluorescent probe may comprise CAACTAGATGCCGCCC (SEQ ID NO:8).

In implementations where the kits quantify the total length of telomeres per copy of genomic DNA, the kit further comprises reagents for determining the number of copy of a housekeeping genes. Thus the kit further comprises a second forward primer and a second reverse primer, wherein the second forward primer and the second reverse primer flank a single-copy housekeeping gene of the genomic DNA. The kit further comprises a fluorescent probe, for example a fluorescent probe that comprises a different fluorophore than that of the MGB fluorescent probe. In some aspects, the housekeeping gene is 36B4. In these embodiments, the second forward primer may comprise CAGCAAGTGGGAAGGTGTAATCC (SEQ ID NO:9) and the second reverse primer may comprise CCCAT-TCTATCATCAACGGGTACAA (SEQ ID NO: 10).

EXAMPLES

The present disclosure is further illustrated by the following examples that should not be construed as limiting. The contents of all references, patents, and published patent applications cited throughout this application, as well as the Figures, are incorporated herein by reference in their entirety for all purposes.

Example 1. Design of the Ω Probe to Calculate Telomere Length

The Ω probe is designed to optimize its application for the calculation of telomere length based on the criteria that accurate calculation of telomere length depends upon successful ligation of the Ω probe in a manner that discriminates the telomere from the sub-telomere DNA. The design of the Ω probe maximizes the number of probes hybridized to adjacent telomere sequences in a conformation that results in circularization of Ω probes upon ligation. FIG. 1 depicts the sequence of the Ω probe along with a diagram of each of its functional components (Panel A) and a 3-dimensional representation of the Ω probe structure prior to ligation (Panel B). The functional components of the Ω probe include in sequential order: (a) the 5'-telomere hybridization arm; (b) the reverse primer binding sequence; (c) the forward primer binding sequence; (d) the TaqMan®-MGB probe sequence and; (e) the 3'-telomere hybridization arm. Sequences in the Ω probe form stabile stem-loop structures to force the hybridization arms to face each other so that multiple probes hybridize in adjacent positions on the telomere (FIG. 2). Upon hybridization with telomeric DNA, the 5'- and 3'-ends of the Ω probe become juxtaposed, and can be ligated to form circular DNA only if there is an exact base-pair match of the dsDNA at the ligation site.

1. Optimizing Ligation and Circularization of Ω Probes in a Manner that Discriminates Against the Sub-Telomere in Order to Calculate Telomere Length.

Human telomeres are composed of (TAAGGG)$_n$ repeat sequences. The telomere region is separated from the gene-containing chromatin by a sub-telomere region. The sub-telomere region is composed of a diverse variety of sequences that randomly and intermittently contains (TXAGGG)$_n$ repeats where x is a variable base, but is most commonly G. To minimize the sub-telomere region in the calculation of telomere length, the hybridization arms of the Ω probe are designed so that the point of ligation of the hybridized arms of the Ω probe occurred at the base that varies in the sub-telomere region. The ligase enzyme requires perfect base pairing at the site of ligation. In the event that a Ω probe hybridizes to a stretch of sub-telomere (TXAGGG)$_n$ repeats, the probability that the variable base will be an A at the ligation site is minimized.

2. Maximizing the Number of Ω Probes Hybridized to Adjacent Telomere Sequences in a Conformation that Result in Circularization Upon Ligation.

The sequences that serve as the reverse PCR primer-binding region and the TaqMan®-MGB probe in the Ω probe are designed to form stabile stem-loop structures to force the hybridization arms to face each other. Incorporation of the stem-loops forces the Ω probe into a conformation that can only hybridize with the telomere in a manner that can be ligated and circularized. These stem-loop structures also facilitate the hybridization of multiple Ω probes to adjacent positions on the telomere (FIGS. 2 and 3). In the absence of the stem-loops, a significant fraction of Ω probes could hybridize incorrectly to the telomere in a manner that is not capable of ligation and circularization. This may return an answer for telomere length that is shorter than the true length. The sequence chosen for the stem-loop was based on thermodynamic stability (ΔG=−10.54 kcal/mol at 37° C.) as determined by M-folding analysis prediction.

Example 2. Optimization of the Ω Probe to Compute the Length of Telomeres

1. Optimization of the 5'-Nuclease qRT-PCR Assay

The Applied Biosystems 7500-fast real-time PCR system (Hercules, CA, USA) was used to perform qRT-PCR assays. In addition to the circularized Ω probe formed upon hybridization with human telomeres, the reaction system included a pair of Ω probe primers, the forward primer (Pf) and the reverse primer (Pr) and a TaqMan®-MGB probe (Table 1). Incorporation of the MGB moiety in the TaqMan® probe is known to enhance its binding strength, which is especially important for primers with the relatively short sequence lengths (12-16 bp) used here.

TABLE 1

| Sequence Name | Sequence | Sequence ID NO: |
|---|---|---|
| 5'-telomere repeat | TTAGGG | n/a |
| 3'-telomere repeat | CCCTAA | n/a |
| 5'-hybridization arm | AACCCTAACCCTAACC | 1 |
| 3'-hybridization arm | CCTAACCCTAACCCT | 2 |
| 1$^{st}$ PCR Pr$^a$ binding | CCGCGCTAGACTAAGCGCTC | 3 |
| 1$^{st}$ PCR Pf$^b$ binding | CAGTGACTCAGCAGCTACCCG | 4 |
| 1$^{st}$ PCR Pf$^b$ | CAGTGACTCAGCAGCTACCCG | 5 |
| 1$^{st}$ PCR Pr$^a$ | GAGCGCTTAGTCTAGCGCG | 6 |
| TaqMan ®-MGB binding region | GGCGGCATCTAGTTGC | 7 |
| TaqMan ®-MGB probe | CAACTAGATGCCGCCC | 8 |
| 2$^{nd}$ PCR Pf$^b$ | CAGCAAGTGGGAAGGTGTAATCC | 9 |
| 2$^{nd}$ PCR Pr$^a$ | CCCATTCTATCATCAACGGGTACAA | 10 |

$^a$forward primer
$^b$reverse primer

2. Optimization of Ω Probe Concentration

Figure 5:
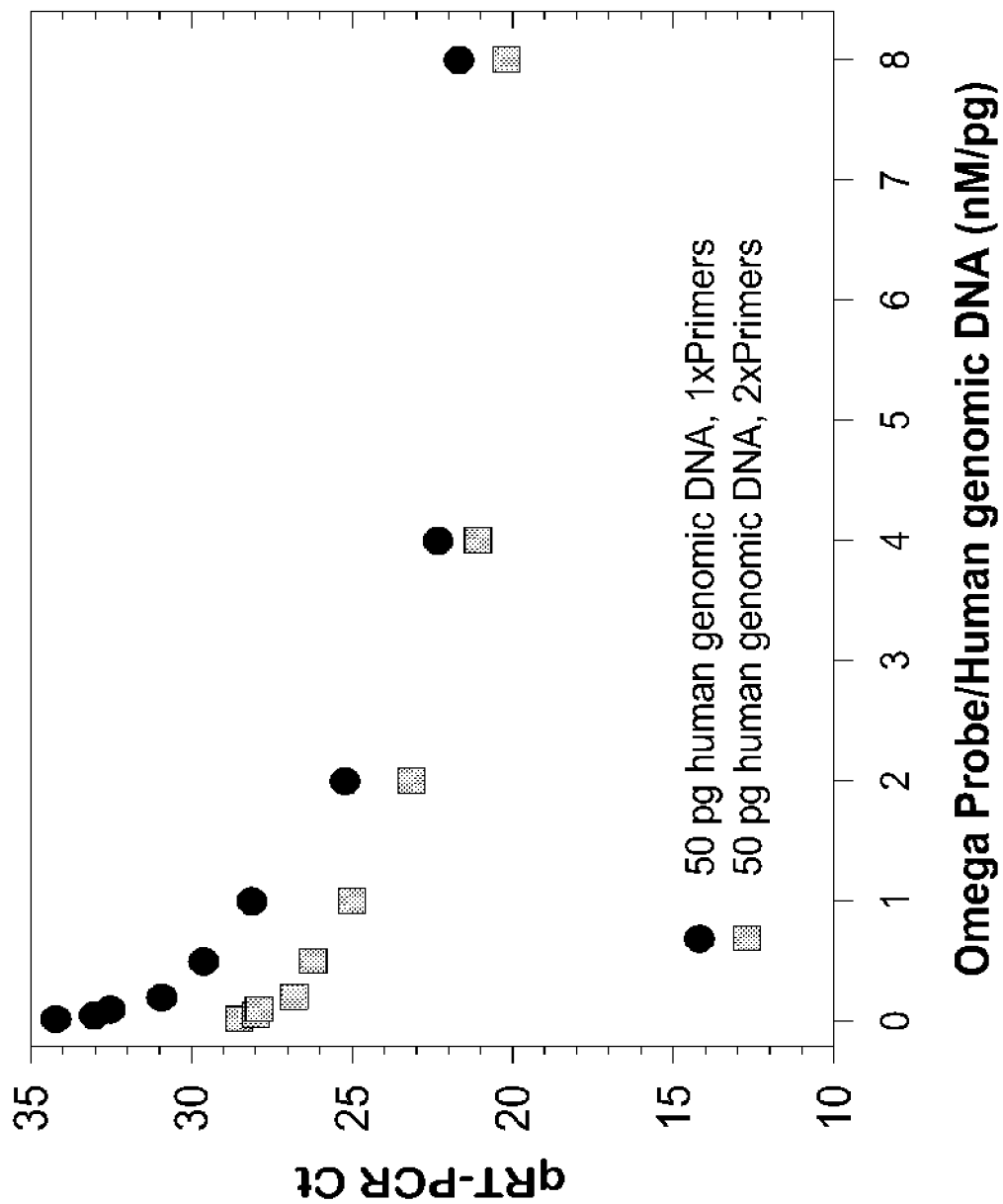
FIG. 5 depicts the number of molecules of circularized nucleic acid probes formed upon hybridization with purified human genomic DNA (represented as Ct) as a function of the ratio of nucleic acid probe to genomic DNA, where Ct is the number of qRT-PCR cycles required for an increase in the fluorescence signal to be detected over that of the mean baseline signal. A minimum value of Ct was observed under each condition when the amount of nucleic acid probe became saturated compared to the available binding sites on the telomeric DNA. At this concentration ratio, bound nucleic acid probes occupied the entire length of the telomere where the calculation of telomere length is made with the greatest accuracy.

To determine the concentration ratio of Ω probes to human genomic DNA that calculates telomere length with greatest accuracy, the hybridization/circularization step was carried out as a function of the amount of Ω probe in the presence of a given amount of human genomic DNA, and the amount of circularized Ω probe generated was quantitated by qRT-PCR (FIG. 5). The number of PCR cycles required for an increase in the fluorescence signal to be detected over that of the mean baseline signal (Ct) decreased quantitatively with an increase in the number of molecules of circularized Ω probe present in the sample. The Ct decreased with increasing amounts of Ω probe until it reached a minimum that was no longer affected by further increases in the ratio of Ω probe to genomic DNA. This defined the ratio of Ω probe to genomic DNA where the amount of Ω probe became saturated under a wide variety of conditions, at which point bound Ω probes occupied the entire length of the telomere where the calculation of telomere length is made with the greatest accuracy. As shown in FIG. 5, in some implementations, at least 4 nM nucleic Ω probe/pg human genomic DNA should be used to quantify the length of telomeres in the genomic DNA sample.

Figure 6:
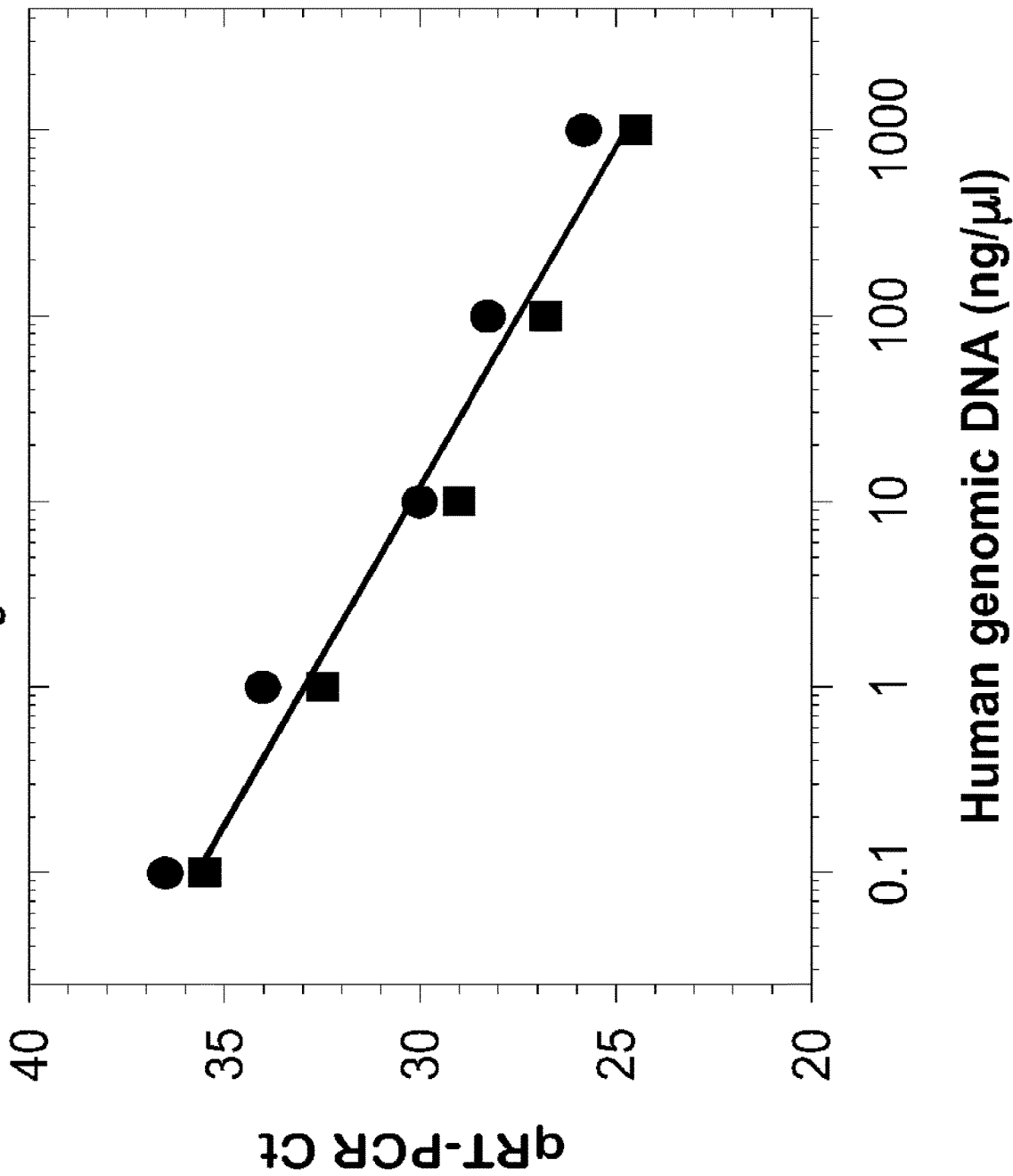
FIG. 6 depicts the Ct versus the amount of the single copy 36B4 gene (specifically the known reference DNA, a housekeeping gene) determined from fluorescence amplification plots of circularized nucleic acid probes as a function of purified human genomic DNA content, where Ct is the number of qRT-PCR cycles required for an increase in the fluorescence signal to be detected over that of the mean baseline signal. The hybridized nucleic acid probes were ligated at 16° C. and these samples were subjected to qRT-PCR after incubation with or without Exo I/III 37° C. for 1 hr. The slope determine by regression of the two replications was −2.82 with $r^2$=0.979.

Example 3. Validation of the Ω Probe Method by Calculating Absolute Telomere Lengths of Four Human Cell Lines 1. Quantitation of Genome Copies A standard curve for a single-copy gene was established in order to calculate absolute telomere length per diploid genome per cell. We selected 36B4, a widely used single-copy housekeeping gene located on chromosome-12 that encodes an acidic ribosomal phosphoprotein. The forward and reverse qRT-PCR primers used were 36B4f and 36B4r with sequences CAGCAAGTGGGAAGGTGTAATCC (SEQ ID NO:9) and CCCATTCTATCATCAACGGGTA-CAA (SEQ ID NO:10), respectively. Amplifications were carried out in duplicate in 20 µl reaction mixture containing 250 nM of 6FAM-TaqMan®-MGB probe. The fast 7500 qRT-PCR instrument was programmed to 58° C. for 30 seconds for both annealing and extension. The plot of the Ct versus the amount of the single copy 35B4 gene (i.e. the known reference DNA) showed a linear dependence on the amount of human DNA when plotted on a log scale (FIG. 6).

The linear correlation between the known SCG genomic DNA and the Ct allows accurate quantification of the copy number of genomes in samples used to calculate telomere length. Since the average quantity of genomic DNA in a human diploid and haploid cell is 6.6 and 3.3 pg, respectively, and a single human cell has 23 pairs of chromosomes, the 36B4 product gives the number of diploid genomes, which enables calculation of telomere length per single cell. The average telomere length of cells is then calculated by dividing total telomere length per genome by 92 telomeres per human diploid cell or by 46 per haploid cell.

2. Ω Probe-Dependent Telomere Length Computation of Human Cell Lines

Figure 7:
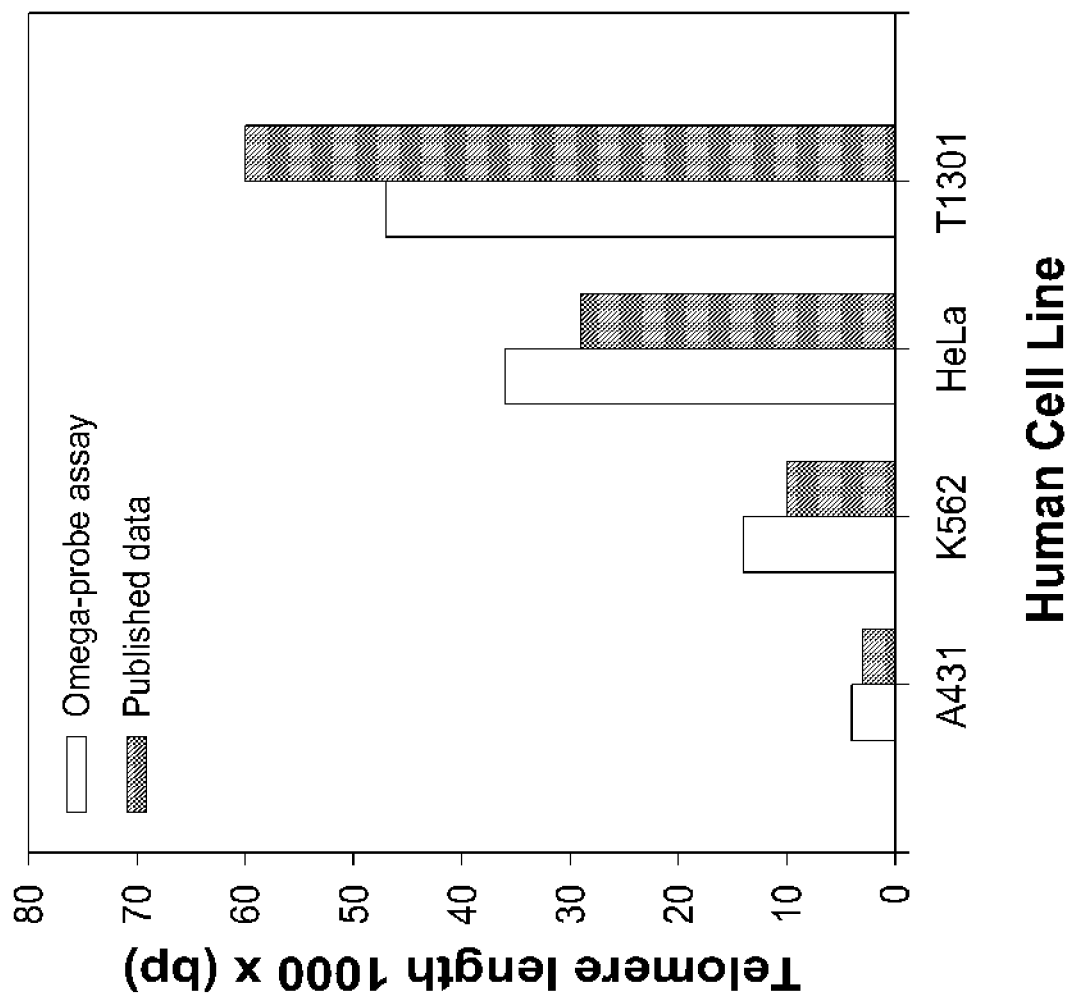
FIG. 7 depicts the lengths of telomeres in purified human DNA from commercially available human cell lines A431, K562, HeLa1211, and TCI 1301 calculated using the Ω probe-mediated approach (open bars) versus published values. These cell lines were chosen because the lengths of telomeres ranged from very short (A431), intermediate (K562 and HeLa1211), to very long (TCI 1301).

Four commercially available human cell lines of known telomere length were chosen to validate the telomere length computation using the Ω probe-mediated approach. The lengths of these telomeres were ~3 kb (very short), 7-10 kb, 16-20 kb, and 60-80 kb (very long), which corresponded to cell lines A431, K562, HeLa1211, and TCI 1301. The telomere lengths of these four human cell lines calculated using the Ω probe approach correlated well with the published values (FIG. 7).

Example 4. Sensitivity of the Ω Probe Assay

1. Measurement of Ct as a Function of the Amount Purified Human Genomic DNA

Figure 8:
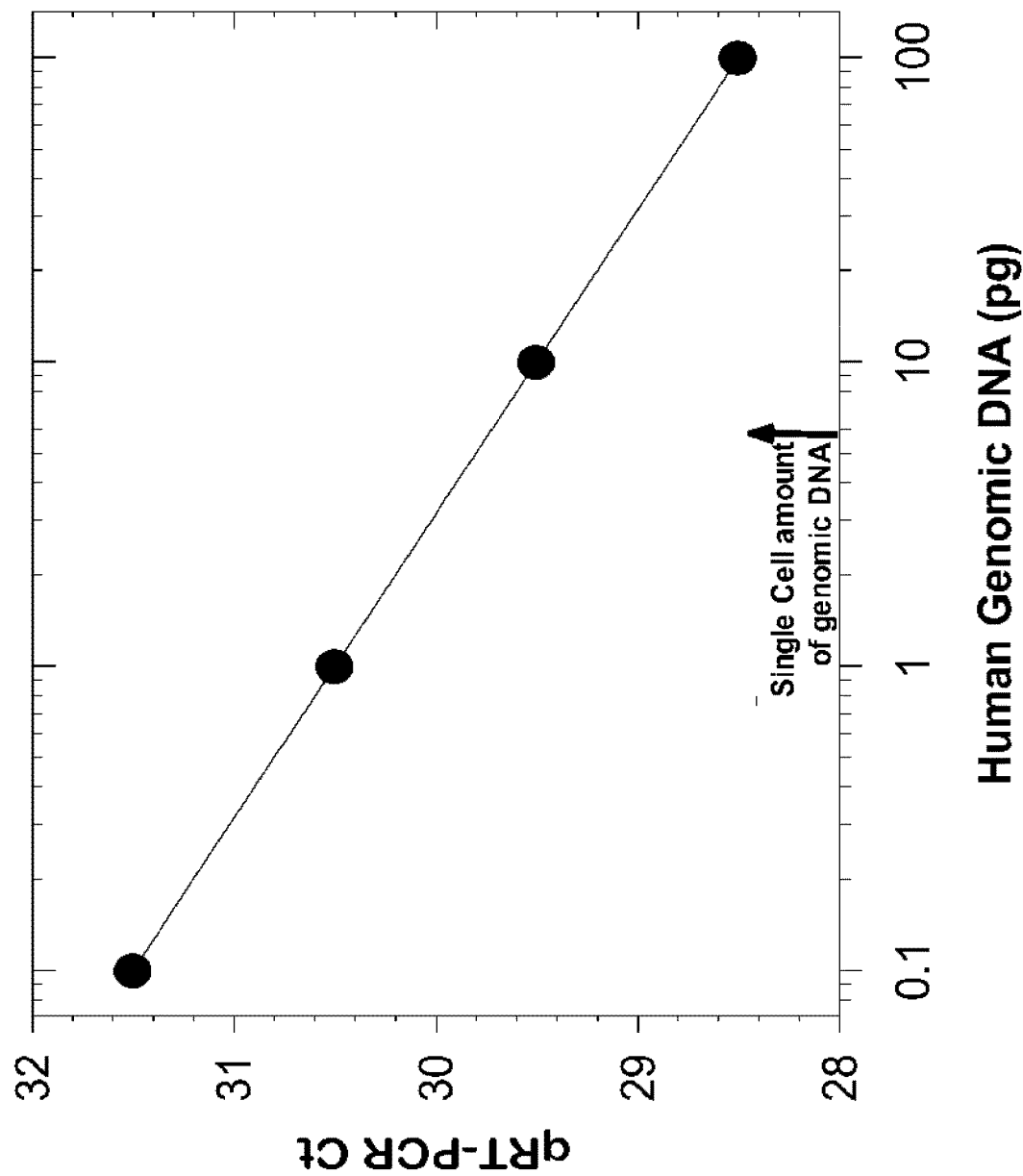
FIG. 8 depicts Ct determined from fluorescence amplification plots of circularized nucleic acid probes as a function of human genomic DNA content, where Ct is the number of qRT-PCR cycles required for an increase in the fluorescence signal to be detected over that of the mean baseline signal. The amount of genomic DNA found in a single typical human cell is 6.6 pg for diploid chromosomes (arrow on x-axis).

The sensitivity of Ω probes to calculate absolute telomere length was evaluated by conducting qRT-PCR assays as a function of the amount of human genomic DNA that hybridized with an optimal amount of Ω probes for hybridization and ligation. FIG. 8 shows that the Ct from circularized Ω probes varied linearly a function of the log of the amount of purified human genomic DNA. The amount of DNA found in a single typical human cell is 6.6 pg for diploid chromosomes (arrow on the x-axis). These results indicate that the Ω probe assay is capable of determining the length of telomeres from the genomic DNA of a single cell.

2. Variation in Ω Probe-Dependent qRT-PCR Among Genomic DNA in Single Cell Lysate Samples.

Figure 9:
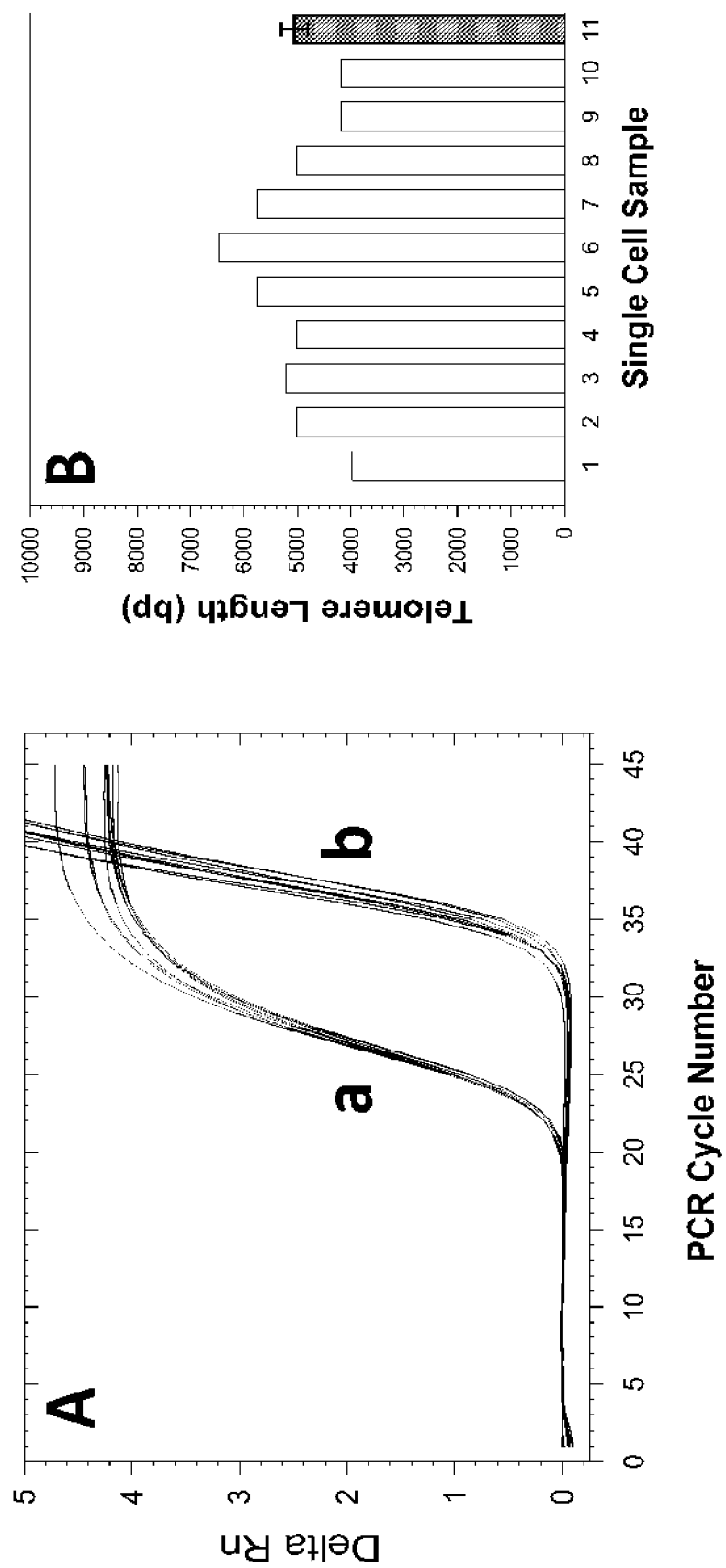
FIG. 9 shows an exemplary calculation of the length of telomeres in a cell. Panel A depicts amplification plots versus PCR amplification cycle number of circularized nucleic acid probes after hybridization to telomeres (a), and the single-copy gene 36B4 (b) from human genomic DNA in the lysate of each of 10 single cells from the cell line CPA. Panel B depicts the length of telomeres calculated for each CPA cell from the data in Panel A.

FIG. 9 shows the fluorescence amplification plots using the Ω probe-dependent qRT-PCR assay of genomic human DNA in the cell lysate from single cells of the HMR-1 human cell line. The presence of a single cell in each of the 10 samples examined was confirmed by microscopy. The signal-to-noise of each replication was consistent, which indicated that the assay was able to provide a quantitative determination of the amount of circularized Ω probe generated. The small variation in the Ct from one cell to another does not imply an error in the measurement, but instead is likely to represent the variation in the telomere lengths from one cell to another. This is significant because tissue samples from cancer patients usually contain a mixture of healthy and malignant cells, each of which may differ significantly in telomere length. The ability to make the calculation on the DNA from each cell would clearly show a difference in telomere length between healthy and malignant cells rather than returning an answer that is the average length for the tissue sample as a whole.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present disclosure is not entitled to antedate such publication by virtue of prior disclosure.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

REFERENCES

Adleman, L. M. (1994). Molecular Computation of Solutions to Combinatorial Problems. Science 266, 1021-1024.

Aubert, G., and Lansdorp, P. M. (2008). Telomeres and aging. Physiological Reviews 88, 557-579.

Baird, D. M., Rowson, J., Wynford-Thomas, D., and Kipling, D. (2003). Extensive allelic variation and ultra-short telomeres in senescent human cells. Nature Genetics 33, 203-207.

Blackburn, E. H. (2000). Telomere states and cell fates. Nature 408, 53-56.

Blackburn, E. H. (2001). Switching and signaling at the telomere. Cell 106, 661-673.

Braich, R. S., Chelyapov, N., Johnson, C., Rothemund, P. W., and Adleman, L. (2002). Solution of a 20-variable 3-SAT problem on a DNA computer. Science 296, 499-502.

Cawthon, R. M. (2002). Telomere measurement by quantitative PCR. Nucleic Acids Research 30.

Ferlicot, S., Youssef, N., Feneux, D., Delhommeau, F., Paradis, V., and Bedossa, P. (2003). Measurement of telomere length on tissue sections using quantitative fluorescence in situ hybridization (Q-FISH). Journal of Pathology 200, 661-666. Goronzy, J. J., Fujii, H., and Weyand, C. M. (2006). Telomeres, immune aging and autoimmunity. Experimental Gerontology 41, 246-251.

Hiyama, E., and Hiyama, K. (2007). Telomere and telomerase in stem cells. Brit J Cancer 96, 1020-1024.

Kahng, A. B., and Reda, S. (2004). Match twice and stitch: a new TSP tour construction heuristic. Operations Research Letters 32, 499-509.

Kari, L., Gloor, G., and Yu, S. (2000). Using DNA to solve the Bounded Post Correspondence Problem. Theor Comput Sci 231, 193-203.

Kimura, M., Stone, R. C., Hunt, S. C., Skurnick, J., Lu, X. B., Cao, X. J., Harley, C. B., and Aviv, A. (2010). Measurement of telomere length by the Southern blot analysis of terminal restriction fragment lengths. Nature Protocols 5, 1596-1607. Lansdorp, P. M., Verwoerd, N. P., vandeRijke, F. M., Dragowska, V., Little, M. T., Dirks, R. W., Raap, A. L., and Tanke, H. J. (1996). Heterogeneity in telomere length of human chromosomes. Human Molecular Genetics 5, 685-691.

Lee, J. Y., Shin, S. Y., Park, T. H., and Zhang, B. T. (2004). Solving traveling salesman problems with DNA molecules encoding numerical values. Biosystems 78, 39-47.

Lee, J. Y., Shin, Soo-Yong, Augh, Sirk June, Park, Tai Hyun and Zhang Byoung-Tak (2003). Temperature Gradient-Based DNA Computing for Graph Problems with Weighted Edges Lecture Notes in Computer Science 2568, 73-84.

Lipton, R. J. (1995). DNA Solution of Hard Computational Problems. Science 268, 542-545.

Macdonald, J., Li, Y., Sutovic, M., Lederman, H., Pendri, K., Lu, W. H., Andrews, B. L., Stefanovic, D., and Stojanovic, M. N. (2006). Medium scale integration of molecular logic gates in an automaton. Nano Letters 6, 2598-2603.

Martens, U. M., Brass, V., Engelhardt, M., Glaser, S., Waller, C. F., Lange, W., Schmoor, C., Poon, S. S. S., and Lansdorp, P. M. (2000). Measurement of telomere length in haematopoietic cells using in situ hybridization techniques. Biochem Soc T 28, 245-250.

Moyzis, R. K., Buckingham, J. M., Cram, L. S., Dani, M., Deaven, L. L., Jones, M. D., Meyne, J., Ratliff, R. L., and Wu, J. R. (1988). A Highly Conserved Repetitive DNA-Sequence, (Ttaggg)N, Present at the Telomeres of Human-Chromosomes. Proceedings of the National Academy of Sciences of the United States of America 85, 6622-6626.

Narath, R., Lorch, T., Greulich-Bode, K. M., Boukamp, P., and Ambros, P. F. (2005). Automatic telomere length measurements in interphase nuclei by IQ-FISH. Cytom Part A 68A, 113-120.

O'Sullivan, J. N., Bronner, M. P., Brentnall, T. A., Finley, J. C., Shen, W. T., Emerson, S., Emond, M. J., Gollahon, K. A., Moskovitz, A. H., Crispin, D. A., et al. (2002). Chromosomal instability in ulcerative colitis is related to telomere shortening. Nature Genetics 32, 280-284.

Ogihara, M., and Ray, A. (1999). Simulating Boolean circuits on a DNA computer. Algorithmica 25, 239-250.

Perner, S., Bruderlein, S., Hasel, C., Waibel, I., Holdenried, A., Ciloglu, N., Chopurian, H., Nielsen, K. V., Plesch, A., Hogel, J., et al. (2003). Quantifying telomere lengths of human individual chromosome arms by centromere-calibrated fluorescence in situ hybridization and digital imaging. American Journal of Pathology 163, 1751-1756.

Qian, L., and Winfree, E. (2011a). Scaling Up Digital Circuit Computation with DNA Strand Displacement Cascades. Science 332, 1196-1201.

Qian, L., and Winfree, E. (2011b). A simple DNA gate motif for synthesizing large-scale circuits. J R Soc Interface 8, 1281-1297.

Qian, L., Winfree, E., and Bruck, J. (2011). Neural network computation with DNA strand displacement cascades. Nature 475, 368-372.

Sakamoto, K., Gouzu, H., Komiya, K., Kiga, D., Yokoyama, S., Yokomori, T., and Hagiya, M. (2000). Molecular computation by DNA hairpin formation. Science 288, 1223-1226.

Spetzler, D., Xiong, F., and Frasch, W. D. (2008). Heuristic Solution to a 10-City Asymmetric Traveling Salesman Problem Using Probabilistic DNA Computing Lecture Notes in Computer Science 4848/2008, 152-160.

Stojanovic, M. N., Mitchell, T. E., and Stefanovic, D. (2002). Deoxyribozyme-based logic gates. Journal of the American Chemical Society 124, 3555-3561.

Tanaka, F., Kameda, A., Yamamoto, M., and Ohuchi, A. (2005). Design of nucleic acid sequences for DNA computing based on a thermodynamic approach. Nucleic Acids Res 33, 903-911.

Vaziri, H., Dragowska, W., Allsopp, R. C., Thomas, T. E., Harley, C. B., and Lansdorp, P. M. (1994). Evidence for a Mitotic Clock in Human Hematopoietic Stem-Cells—Loss of Telomeric DNA with Age. Proceedings of the National Academy of Sciences of the United States of America 91, 9857-9860.

Wang, F., Pan, X. H., Kalmbach, K., Seth-Smith, M. L., Ye, X. Y., Antumes, D. M. F., Yin, Y., Liu, L., Keefe, D. L., and Weissman, S. M. (2013). Robust measurement of telomere length in single cells. Proceedings of the National Academy of Sciences of the United States of America 110, E1906-E1912.

Willeit, P., Willeit, J., Mayr, A., Weger, S., Oberhollenzer, F., Brandstatter, A., Kronenberg, F., and Kiechl, S. (2010). Telomere Length and Risk of Incident Cancer and Cancer Mortality. Jama-J Am Med Assoc 304, 69-75.

Xie, Z., Wroblewska, L., Prochazka, L., Weiss, R., and Benenson, Y. (2011). Multi-Input RNAi-Based Logic Circuit for Identification of Specific Cancer Cells. Science 333, 1307-1311.

Xiong, F. S., and Frasch, W. D. (2011). Padlock probe-mediated qRT-PCR for DNA computing answer determination. Nat Comput 10, 947-959.

Xiong, F. S., Spetzler, D., and Frasch, W. D. (2009). Solving the fully-connected 15-city TSP using probabilistic DNA computing. Integrative Biology 1, 275-280.

Zhu, H. D., Belcher, M., and van der Harst, P. (2011). Healthy aging and disease: role for telomere biology? Clin Sci 120, 427-440.46. Stricker, J. et al. A fast, robust and tunable synthetic gene oscillator. Nature 456, 516-519 (2008).

Payne, S. et al. Temporal control of self-organized pattern formation without morphogen gradients in bacteria. Mol. Syst. Biol. 9, 697 (2013).

Wu, M. et al. Engineering of regulated stochastic cell fate determination. Proc. Natl. Acad. Sci. 201305423 (2013). doi:10.1073/pnas.1305423110

St-Pierre, F. et al. One-Step Cloning and Chromosomal Integration of DNA. ACS Synth. Biol. 2, 537-541 (2013).

Mahalakshmi, S., Sunayana, M. R., SaiSree, L. & Reddy, M. yciM is an essential gene required for regulation of lipopolysaccharide synthesis in *Escherichia coli*. Mol. Microbiol. 91, 145-157 (2014).

What is claimed:

1. A nucleic acid probe for the detection of a region of DNA, the probe comprising:
a 5' hybridization arm;
a reverse PCR primer binding region;
a forward PCR primer region;
a minor groove binding (MGB) probe region; and
a 3' hybridization arm,
wherein the sequences of the reverse PCR primer binding region and the MGB probe region each form a stem loop, and the 5' hybridization arm and 3' hybridization arm are complementary to adjacent regions in the region in DNA.

2. The nucleic acid probe of claim 1, wherein the region of DNA is a repeated region of DNA.

3. A method of determining the copy number of a region of DNA in a DNA sample, the method comprising:
hybridizing the nucleic acid probe of claim 1 to the DNA sample, wherein the 5' hybridization arm and the 3' hybridization arm of the nucleic acid probe are hybridized to adjacent regions on the DNA sample;
ligating the 5' hybridization arm to the 3' hybridization arm of the nucleic acid probe to form a circularized DNA; and
quantifying the number of circularized DNA, wherein the number of circularized DNA correlates to the copy number of the region of DNA in the DNA sample.

4. The method of claim 3, further comprising removing unligated nucleic acid probe prior to quantifying the number of circularized DNA.

5. The method of claim 4, wherein the step of removing unligated nucleic acid probe comprises digesting unligated nucleic acid probe with an exonuclease.

6. The method of claim 4, wherein the region of DNA is a repeated region of DNA.

7. The method of claim 6, wherein the DNA sample is from a single cell.

8. A method of determining the length of a region of tandem repeats in a DNA sample, the method comprising:
hybridizing a nucleic acid probe to the DNA sample, the nucleic acid probe comprising:
a 5' hybridization arm;
a reverse PCR primer binding region;
a forward PCR primer region;
a minor groove binding (MGB) probe region; and
a 3' hybridization arm,
wherein the sequences of the reverse PCR primer binding region and the MGB probe region each form a stem loop and the 5' hybridization arm and the 3' hybridization arm of the nucleic acid probe are hybridized to adjacent regions in the region of tandem repeats in DNA;
ligating the 5' hybridization arm to the 3' hybridization arm of the nucleic acid probe to form a circularized DNA; and
quantifying the number of circularized DNA, wherein the number of circularized DNA correlates to the length of the region of tandem repeats in the DNA sample.

9. The method of claim 8, wherein quantifying the amount of circularized DNA comprises:
conducting a first quantitative real-time PCR (qRT PCR) reaction with a first qRT-PCR reaction mixture to calculate a Ct value for the first qRT-PCR reaction, wherein the first reaction mixture comprises:
a first forward primer;
a first reverse primer;
a quantification sample, wherein the quantification sample is the linear complement to the circularized DNA extended using the first reverse primer, the quantification sample comprises the reverse complement of:
the forward primer region of the nucleic acid probe;
the MGB probe region of the nucleic acid probe;
the 3' hybridization arm of the nucleic acid probe;
the 5' hybridization arm of the nucleic acid probe; and
the reverse PCR primer-binding region of the nucleic acid probe; and
a fluorescent probe,
wherein the first forward primer binds to the reverse complement of the forward primer region of the nucleic acid probe, the first reverse primer binds to the reverse primer binding region, and the fluorescent probe comprises a fluorophore at the 5' end and an MGB nonfluorescent quencher (MGBNFQ) at the 3' end and binds to the MGB probe region;
determining the amount of the circularized DNA based on the Ct value of the first qRT-PCR reaction;
conducting a second qRT-PCR reaction on the DNA sample with a second qRT-PCR reaction mixture to calculate a Ct value for the second qRT-PCR reaction, wherein the second qRT-PCR reaction mixture comprises:
a second forward primer;
a second reverse primer; and
the fluorescent probe,
wherein the second forward primer and the second reverse primer flank a known reference DNA;
determining the amount of the known reference DNA in the DNA sample based on the Ct value of the second qRT-PCR reaction thereby calculating the number of copies of the known reference DNA in the DNA template source; and
calculating the length of the region of tandem repeats in a DNA sample from the number of copies of the known reference DNA and the amount of circularized DNA.

10. The method of claim 8, further comprising removing unligated nucleic acid probe prior to quantifying the number of circularized DNA.

11. The method of claim 10, wherein the step of removing unligated nucleic acid probe comprises digesting unligated nucleic acid probe with an exonuclease.

12. The method of claim 8, wherein the DNA sample is from a single cell.

13. The method of claim 9, wherein the fluorophore is selected from the group consisting of 6FAM, VIC, NED, Cy5, and Cy3.

14. The method of claim 8, wherein the region of tandem repeats in DNA is a telomere.

15. The method of claim 14, wherein the region of the telomere to which the 5' hybridization arm and 3' hybridization arm is complementary comprises at least six repeats of TTAGGG.

16. The method of claim 14, wherein the fluorescent probe comprises an oligonucleotide sequence of GCAACTAGATGCCGCC (SEQ ID NO:13).

17. The method of claim 14, wherein the first forward primer comprises CAGTGACTCAGCAGCTACCCG (SEQ ID NO:5).

18. The method of claim 14, wherein the first reverse primer comprises GAGCGCTTAGTCTAGCGCG (SEQ ID NO:6).

19. The method of claim 14, wherein the ratio of the nucleic acid probe to the DNA template source is at least 4 nM nucleic acid probe per 1 pg DNA template source.

20. A kit for quantifying a region of DNA comprising:
the nucleic acid probe of claim 1;
a forward primer;
a reverse primer; and
a MGB fluorescent probe.

* * * * *

SEQUENCE LISTING

<160> NUMBER OF SEQ ID NOS: 14

<210> SEQ ID NO 1
<211> LENGTH: 16
<212> TYPE: DNA
<213> ORGANISM: Artificial Sequence
<220> FEATURE:
<223> OTHER INFORMATION: 5' hybridization arm sequence

<400> SEQUENCE: 1
aaccctaacc ctaacc                                                      16

<210> SEQ ID NO 2
<211> LENGTH: 15
<212> TYPE: DNA
<213> ORGANISM: Artificial Sequence
<220> FEATURE:
<223> OTHER INFORMATION: 3' hybridization arm sequence

<400> SEQUENCE: 2 cctaaccta accct                                                        15

<210> SEQ ID NO 3
<211> LENGTH: 20
<212> TYPE: DNA
<213> ORGANISM: Artificial Sequence
<220> FEATURE:
<223> OTHER INFORMATION: first reverse primer binding sequence

<400> SEQUENCE: 3
ccgcgctaga ctaagcgctc                                                  20

<210> SEQ ID NO 4
<211> LENGTH: 21
<212> TYPE: DNA
<213> ORGANISM: Artificial Sequence
<220> FEATURE:
<223> OTHER INFORMATION: first forward primer binding sequence

<400> SEQUENCE: 4
cagtgactca gcagctaccc g                                                21

<210> SEQ ID NO 5
<211> LENGTH: 21
<212> TYPE: DNA
<213> ORGANISM: Artificial Sequence
<220> FEATURE:
<223> OTHER INFORMATION: first forward primer

<400> SEQUENCE: 5
cagtgactca gcagctaccc g                                                21

<210> SEQ ID NO 6
<211> LENGTH: 19
<212> TYPE: DNA
<213> ORGANISM: Artificial Sequence
<220> FEATURE:
<223> OTHER INFORMATION: first reverse primer

<400> SEQUENCE: 6
gagcgcttag tctagcgcg                                                   19

<210> SEQ ID NO 7
<211> LENGTH: 16
<212> TYPE: DNA
<213> ORGANISM: Artificial Sequence

```
<220> FEATURE:
<223> OTHER INFORMATION: MGB binding sequence

<400> SEQUENCE: 7
ggcggcatct agttgc                                              16

<210> SEQ ID NO 8
<211> LENGTH: 16
<212> TYPE: DNA
<213> ORGANISM: Artificial Sequence
<220> FEATURE:
<223> OTHER INFORMATION: MGB probe

<400> SEQUENCE: 8
caactagatg ccgccc                                              16

<210> SEQ ID NO 9
<211> LENGTH: 23
<212> TYPE: DNA
<213> ORGANISM: Artificial Sequence
<220> FEATURE:
<223> OTHER INFORMATION: second forward primer

<400> SEQUENCE: 9
cagcaagtgg gaaggtgtaa tcc                                      23

<210> SEQ ID NO 10
<211> LENGTH: 25
<212> TYPE: DNA
<213> ORGANISM: Artificial Sequence
<220> FEATURE:
<223> OTHER INFORMATION: second reverse primer

<400> SEQUENCE: 10
cccattctat catcaacggg tacaa                                    25

<210> SEQ ID NO 11
<211> LENGTH: 16
<212> TYPE: DNA
<213> ORGANISM: Artificial Sequence
<220> FEATURE:
<223> OTHER INFORMATION: fluorescent probe

<400> SEQUENCE: 11
gcaactagat gccgcc                                              16

<210> SEQ ID NO 12
<211> LENGTH: 88
<212> TYPE: DNA
<213> ORGANISM: Artificial Sequence
<220> FEATURE:
<223> OTHER INFORMATION: probe

<400> SEQUENCE: 12
aaccctaacc ctaaccccgc gctagactaa gcgctccagt gactcagcag ctacccggca     60
actagatgcc gcccctaacc ctaaccct                                       88

<210> SEQ ID NO 13
<211> LENGTH: 80
<212> TYPE: DNA
<213> ORGANISM: Homo sapiens

<400> SEQUENCE: 13
ggttagggtt agggttaggg ttagggttag ggttagggtt agggttaggg ttagggttag     60
```

```
ggttagggtt agggttaggg                                              80

<210> SEQ ID NO 14
<211> LENGTH: 32
<212> TYPE: DNA
<213> ORGANISM: Artificial Sequence
<220> FEATURE:
<223> OTHER INFORMATION: omega probe

<400> SEQUENCE: 14
ccaatcccaa tcccaatccc aatcccaatc cc                                32
```